US006008159A

United States Patent [19]
Medd et al.

[11] Patent Number: 6,008,159
[45] Date of Patent: Dec. 28, 1999

[54] CONTROL OF ANNUAL GRASS WEEDS

[75] Inventors: Richard William Medd, Orange; Mathew Alexander Campbell, Epping, both of Australia

[73] Assignee: Minister of Agriculture for the State of New South Wales, New South Wales, Australia

[21] Appl. No.: 08/877,578

[22] Filed: Jun. 17, 1997

[51] Int. Cl.[6] .............................. A01N 43/40; C12N 1/14

[52] U.S. Cl. ........................................ 504/177; 435/254.1

[58] Field of Search .......................... 504/117; 435/254.1

[56] References Cited

U.S. PATENT DOCUMENTS 5,491,122 2/1996 Manker et al. ......................... 504/100

5,498,624 3/1996 McLoughlin et al. .................. 514/406

5,837,685 11/1998 Strobel et al. ............................ 514/15

*Primary Examiner*—Shelley A. Dodson
*Assistant Examiner*—Alton Pryor
*Attorney, Agent, or Firm*—Nixon & Vanderhye

[57] ABSTRACT

Method for controlling the proliferation of annual grass weeds in an area by applying to the area a composition of one or more species of Pyrenophora fungi or anamorphs thereof, or a toxin or toxin-containing preparation derived from one or more species of Pyrenophora fungi or anamorphs thereof in association with an agriculturally acceptable carrier.

22 Claims, 7 Drawing Sheets

CONTROL OF ANNUAL GRASS WEEDS

This invention relates to methods and compositions for the control of annual grass weeds, especially annual ryegrass, brome species, barley grass and vulpia.

Weeds are the major pest of the Australian grain industry. The cost of weed control, the increased reliance on herbicides and the development of resistance in weeds to herbicides, are major concerns. As a result, the industry is increasingly looking to biological control agents and methods. However, a major constraint of biological control, particularly for annual grass weeds, is their close genetic affinity with winter cereals. This precludes, for example, the importation of exotic agents because of quarantine safeguards.

Weed control has historically concentrated on achieving plant mortality. However, it is now recognised that seed production and replenishment of the seed bank are the main factors driving the persistence of weeds that have short lived seeds. Nevertheless, there are currently no methods for directly controlling seed production of weeds in grain crops. One possibility for reducing seed production is the exploitation of pathogenic seed fungi which is now conceivable using a mycoherbicide approach (Medd, 1992).

The present inventors selected the seed borne fungus *Pyrenophora semeniperda* (Brittleb, & D. B. Adam) Shoemaker (anamorph *Drechslera campanulata* (Lév.) B. Sutton as a candidate fungus for the control of annual grass weeds. Whilst having a broad host range and distribution, this fungus is considered to be of negligible economic importance on winter cereals, particularly wheat, either as a leaf spotting or seedling blight organism or as a seed pathogen. The results hereinafter show, for the first time, that this fungus can be utilised to affect seed viability and thereby control annual grass weeds.

Thus, in a first aspect, the present invention provides a method for controlling the proliferation of annual grass weeds in an area, comprising applying to said area a composition comprising:

(i) one or more species of Pyrenophora fungi and/or their anamorphs, and/or (ii) a toxin(s) or toxin(s)-containing preparation derived from one or more species of Pyrenophora fungi and/or their anamorphs; and an agriculturally acceptable carrier.

Where the composition comprises Pyrenophora fungus or fungi rather than a toxin(s) or toxin(s)-containing preparation, it is preferred that the fungus be in the form of conidia, although hyphae and mycelia are also suitable. In compositions comprising conidia, it is preferred that the compositions are conidial suspensions of about $1 \times 10^3$ to $8 \times 10^4$ conidia $ml^{-1}$, more preferably about $2.5 \times 10^4$ to $7.5 \times 10^4$ conidia $ml^{-1}$. Compositions comparing mycelia preferably include about 250 g $L^{-1}$ of a mycelial homogenate having an effective concentration of mycelium fragments, and said compositions may be encased in a dissolvable solid carrier such as alginate. Compositions comprising hyphae preferably include about 25 g $L^{-1}$ hyphae. These compositions may be applied (e.g. sprayed) to the area at amounts of 250 ml $m^{-2}$.

The present inventors have also found that seed infection is maximised when the composition of Pyrenophora fungus or fungi is applied whilst the grass is in anthesis. Thus, it is preferred that the composition be applied when 35% (preferably 50%) or more of the total annual grass weeds, or at least 35% (preferably 50%) or more of any one target annual grass weed species, in the area are in anthesis (GS 55 to GS 75), or more preferably, the middle of anthesis (GS 65 to GS 70).

It is preferred that the Pyrenophora fungi(us) is *P. semeniperda*, *P. teres* or a mixture thereof. Similarly, it is preferred that the toxin(s) or toxin(s)-containing preparation is derived from *P. semeniperda*, *P. teres* or a mixture thereof.

The area may, of course, include a grain crop such as wheat. In such circumstances, it is preferable that the composition be applied to the area when the crop plants have reached an adult stage, since the crop plants show greater resistance to infection at the stage.

Preferably, the method of the first aspect is applied for the control of proliferation of annual grass weeds selected from the group consisting of annual ryegrass, brome species, wild oats, barley grass and vulpia.

The inventors have also identified a particular isolate (DAR71761) of *P. semeniperda* which appears to be substantially more pathogenic than other isolates tested. It is therefore also preferred that the *P. semeniperda* utilised in the composition and/or the production of toxin(s) or toxin (s)-containing preparation, is isolate DAR71761.

Isolate DAR71761 has been deposited with NSW Agriculture Plant Pathology Herbarium, Agricultural Research and Veterinary Centre, Orange. A deposit of isolate DAR71761 has also been made in accordance with the "Budapest Treaty" with AGAL, Pymble, NSW, Australia. This latter deposit was made on Jan. 10, 1996 and has been accorded the accession No. 96/2220.

It is further preferred that the composition comprises a surfactant(s) and/or a wetting agent(s).

In a second aspect, the present invention provides a composition for use in the method of the first aspect, the composition comprising:

(i) one or more species of Pyrenophora fungi and/or their anamorphs, and/or (ii) a toxin(s) or toxin(s)-containing preparation derived from one or more species of Pyrenophora fungi and/or their anamorphs; and an agriculturally acceptable carrier.

As indicated above, the method of the first aspect may utilise a Pyrenophora toxin(s) or toxin(s)-containing preparation. The present inventors are the first to provide such toxin preparations from Pyrenophora.

Thus, in a third aspect, the present invention provides a toxin(s)-containing preparation derived from Pyrenophora. Particularly, the present invention provides a toxin(s)-containing filtrate derived from *P. semeniperda*, *P. teres* or a mixture thereof.

In a further aspect, the present invention provides a method for producing a Pyrenophora toxin(s) or toxin(s)-containing preparation comprising, growing one or more species of Pyrenophora fungi and/or their anamorphs in culture with agitation.

Preferably, the Pyrenophora fungi(us) is *P. semeniperda*, *P. teres* or a mixture thereof.

The invention will be hereinafter further described with reference to the following non-limiting examples and accompanying figures.

Figure 1:
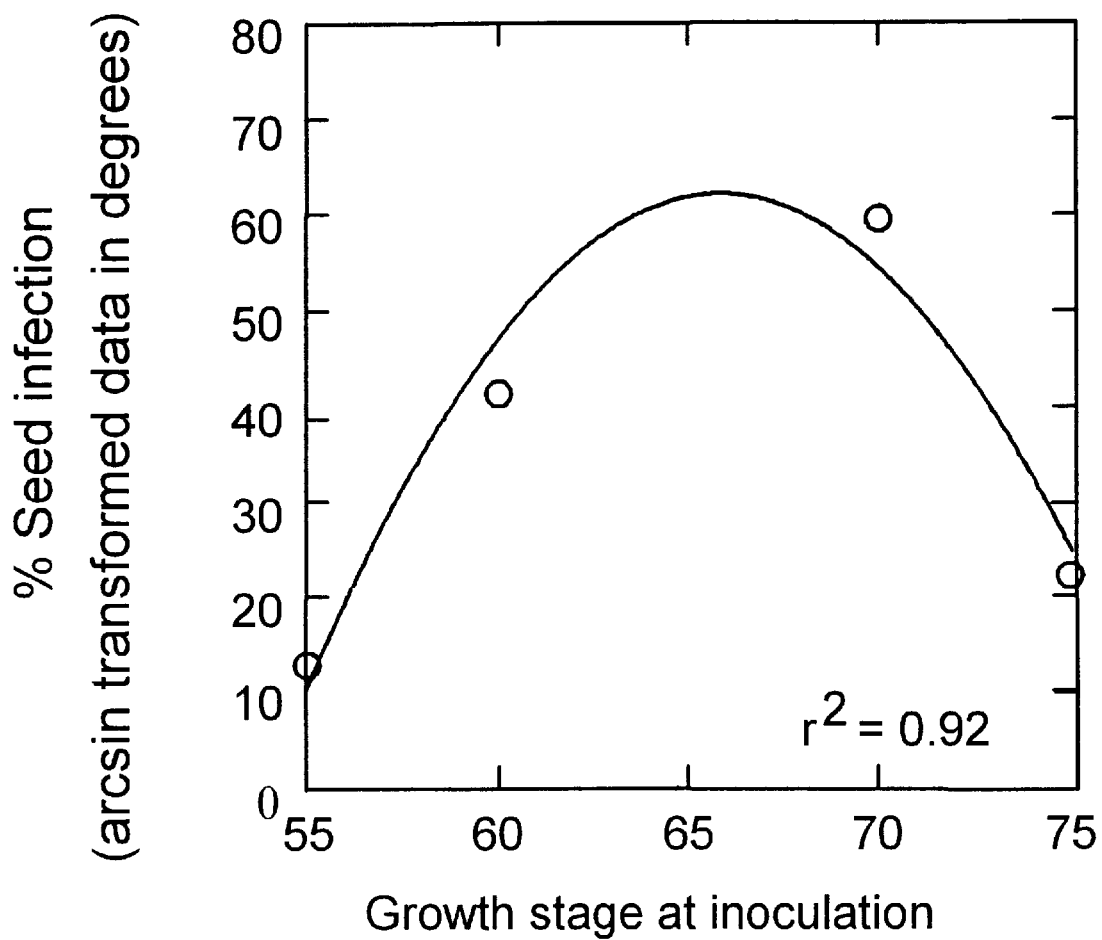
FIG. 1: Provides a graph showing infection of mature wheat seeds by *P. semeniperda* (isolate DAR71761) inoculated at 4 different stages of development according to the scale of Zadoks, et al., (1974). Data are means of 10 replicates each with 100 observations. The regression equation is (arcsin $\sqrt{Y}$)=$1.8 \times 10^3 + 58X - 0.44X^2$, where Y=proportion of mature seeds infected by *P. semeniperda* and X=growth stage of plants at inoculation.

GENERAL MATERIALS AND METHODS (1) Maintaining Cultures of Pathogens

Source, storage and maintenance of isolates.

Isolates of P. semeniperda were obtained from the culture collection held at the New South Wales Agricultural Research & Veterinary Centre, Orange NSW, Australia. Isolates of P. teres were obtained from the Queensland Department of Primary Industry, Plant Pathology Culture collection held at Brisbane Qld, Australia (Table 1).

TABLE 1

Details of isolates of P. semeniperda and P. teres used herein.

| Species | Isolate No. | Host Plant | Place of Collection | Date |
| --- | --- | --- | --- | --- |
| P. semeniperda | 580681 | Avena ludoviciana | Wagga Wagga, NSW | 25/11/89 |
| P. semeniperda | 580129 | Vulpia bromoides | Angaston, SA | 8/11/84 |
| P. semeniperda | 580148 | Avena sativa | Coonalpyn, SA | 9/11/84 |
| P. semeniperda | 580170 | Hordeum vulgare | Donald, SA | 9/11/84 |
| P. semeniperda | 580520 | Chloris truncata | York, WA | 15/8/86 |
| P. semeniperda | 580534 | Triticum aestivum | Corrigon, WA | 15/8/86 |
| P. semeniperda | 580584 | Lolium perenne | Cervantes, WA | 22/8/86 |
| P. teres | W.I.1535 | Hordeum vulgare | Allora, Qld | 12/4/87 |
| P. teres | W.I.8712 | Hordeum vulgare | Brisbane, Qld | 9/6/77 |

*580681 is the isolate DAR71761

P. semeniperda isolates were received in evacuated glass ampoules, and the P. teres isolates were received in small glass slants. On receipt of isolates, the ampoules were opened and the fungal material was placed on Petri plates containing potato dextrose agar (PDA). After 14 days incubation under laboratory conditions (15 to 25° C.) 20 three mm cores of fungus and PDA were cut from the growing edge of each different isolates' colony. The cores were placed in ampoules and freeze-dried under partial vacuum. They were then sealed with a gas blow torch. A sample of each freeze-dried isolate was re-plated onto PDA to establish that the fungal material was still viable after undergoing the freeze-drying process. Isolates were freeze-dried to ensure that an adequate supply of original isolate material was available if a particular isolate lost pathogenicity or vigour after repeated sub-culturing. Ampoules were stored in the dark at room temperature.

Monoconidial isolates of each accession were maintained as stock cultures on modified alphacel medium (MAM, consisting of oatmeal, 10 g; $MgSO_4 \cdot 7H_2O$, 1 g; $KH_2PO_4$, 1.5 g; $NaNo_3$, 1 g; coconut milk, 50 ml; agar, 17 g; distilled $H_2O$ 1 L) at room temperature (15 to 25° C.) with a 12 hour photoperiod under near ultra-violet light (320–420 nm, 36.5 $\mu mol\ m^{-2}s^{-1}$) supplied by 2×40 W Osram cool white and 2×40 W Hitachi black light fluorescent tubes positioned 40 cm above the Petri plates. In an attempt to reduce genetic variability, stock cultures were periodically sub-cultured using a single conidium as inoculum. Triticum aestivum wheat seedlings were regularly inoculated with conidia derived from stock cultures, and P. semeniperda was re-isolated from leaf spot lesions in order to maintain isolate pathogenicity.

Preparation of media and cultures.

All culture media used were prepared immediately prior to use. Media used in all studies were autoclaved for 30 minutes at 103 kPa (121° C.). Unless otherwise stated, 15 ml portions of agar media were dispensed in 90 mm diameter plastic Petri plates using a repetitive syringe (Becton, Dickinson & Co., USA). Portions (125 ml) of liquid culture media were dispensed into 250 ml capacity borosilicate screw top bottles prior to autoclaving. Petri plates and liquid culture bottles were always inoculated with a 3 mm diameter piece of mycelium and agar excised from the growing edge of 7 day old monoconidial stock culture. Petri plates were sealed with Parafilm® to reduce water loss and to prevent contamination.

(2) Maintenance of Host Material

Source of seed.

Seeds were obtained from the Department of Botany, Seed Collection, University of New England. Seeds of the spring wheat cultivar 'Cook' were used in all experiments unless otherwise stated. Seed of both wheat and Bromus diandrus (February to April 1992), and in field plots grown in pots in the glasshouse (February to April 1992), and in field plots grown at the University of New England's farm 'Laureldale' in the winter season of 1992. The seed produced by plants grown in the field plots was used in all the experimental work requiring host material after 1992.

Plant Production.

All seeds were sown into a potting mix consisting of equal amounts (v/v) of sieved (4 mm aperture) river sand and vermiculite contained in one of three different pot types. For experiments requiring seedling leaf material, 5 seeds were sown into potting mix contained in 240 ml volume polystyrene cups which had a 5 mm diameter hole drilled out of the bottom. For experiments requiring older leaf material and plants in flower, 3 seeds were sown into potting mix contained in a 1000 ml volume plastic container which had a 5 mm diameter hole drilled out of the bottom. Eleven g of slow release fertilizer (Osmocote, 2–3 month) was added to the surface of each pot. The plants grown in 1000 ml capacity pots were thinned to one per pot at approximately 21 days after sowing. For field experiments, seed were sown into potting mix contained in 64 cell (8×8, Kwik Pots®) seedling trays. After sowing, pots were immediately watered to approximate field water holding capacity. Pots were watered every two days after seedling emergence. In addition, a liquid fertiliser was applied once a week (Aquasol®). All plants were grown in a glasshouse where temperatures ranged from 8 to 15° C. minimum and 15 to 25° C. maximum.

(3) Inoculum Production

Isolates of *P. semeniperda* were grown on MAM and were initiated by inoculating Petri plates from monoconidial stock cultures. Petri plates were not sealed with Parafilm®. Petri plates were incubated under the same conditions as described in section (1). Seven days after inoculation, the colonies grown on Petri plates were wounded either by cutting through the mycelium and agar with a sterile stainless steel 3 mm diameter cork borer or by slashing through the mycelium and agar with a sterile scalpel (wound size ranged from 3 to 7 mm between slashes). This procedure was repeated until the whole colony had been wounded. The wounded colonies in Petri plates were the replaced under the same incubation conditions for a further 7 days.

After the full 14 day incubation period, conidial suspensions were prepared using one of the following methods. Conidial suspensions were always prepared immediately before use unless otherwise stated and kept refrigerated to prevent conidial germination. The first method was developed because it allowed for the maximal removal of conidia from the conidiophores when large volumes of inoculum was required for field studies. The second method was used to produce smaller volumes of conidial suspension for glasshouse based studies.

Method 1: Five wounded cultures and their agar medium were removed from the Petri plates and placed into a 500 ml capacity screw top bottle containing 250 ml of refrigerated sterile distilled water. The bottle containing the cultures was shaken vigorously for 2 to 3 minutes by hand to remove conidia from their conidiophores. The resultant suspension was then filtered through a series of stainless steel laboratory sieves to a final size of less than 63 $\mu$m to remove agar and mycelial fragments. The number of conidia in the suspension was determined by counting the conidia in 50 cell units (100×magnification light microscopy) within a Sedgewick Rafter counting cell (Graticules Limited, England) and multiplying the result by 20 to give a final concentration in conidia $ml^{-1}$. Dilutions of suspensions were made when high densities of conidia reduced the accuracy of the technique.

Method 2: Twenty of 30 ml of refrigerated sterile distilled water was added to each wounded culture contained in Petri plates. The whole wounded colony was scraped gently with the blunt side of a scalpel blade and the resultant suspension was filtered through a series of stainless steel laboratory sieves to a final size of less than 63 $\mu$m to remove agar and mycelial fragments. The number of conidia $ml^{-1}$ in the suspension was determined using a Sedgewick Rafter counting cell and the wetting agent Pulse® was added to the suspension (0.01% by volume).

(4) Inoculation and Incubation Techniques

Plants were removed from the glasshouse just prior to inoculation. Inoculum was atomised onto host plants by a hand operated applicator (Canyon) until run-off of inoculum occurred. Wheat and bromegrass flowers were inoculated by dipping the spikelets into a conidial suspension. After inoculation plants were immediately placed into a chamber housed within a controlled environment growth cabinet and fitted with an ultrasonic humidifier to provide a dew period. In some experiments, an environment of high humidity was created for inoculated wheat and bromegrass spikelets by placing a plastic bag over the flowering head and fastening it with a paper clip. In some experiments, adult leaves were inoculated by placing a 100 $\mu$l drop of conidial suspension on a leaf held between 2 cover slips (22×22 mm) and secured with a paper clip.

All field inoculations were carried out after 2100 hours. The reasons for this were three-fold: firstly, the temperatures were cooler and the chances of the inoculum becoming desiccated were slight, secondly, the chances of 'spray drift' were lower since the wind was negligible after sunset, and thirdly, on most inoculation nights dew formation had already occurred, thus ensuring a post-inoculation dew period. Field plots were sprayed using a pressure sprayer or a hand-held $CO_2$ propelled spray gun (Badger Air Brush Co., Illinois, USA).

(5) Disease Assessment

Lesion development.

The level of disease that developed on leaves inoculated with a conidial suspension was assessed visually in two ways. Firstly, the number of lesions that had developed was counted on each leaf assessed, and secondly, the necrotic area of each lesion was given a size rating of between 1 and 4 based on the scale shown below:

1. Less than 1 mm in diameter
2. Between 1 and 5 mm in diameter
3. Between 5 and 10 mm in diameter
4. Greater than 10 mm in diameter The level of disease that developed on leaves following inoculation with toxic filtrates was assessed visually and allocated a number between 1 and 5 based on the disease rating scale shown below;

1. No symptoms
2. Chlorosis only
3. Chlorosis and slight necrosis
4. Necrosis and slight chlorosis
5. Necrosis only The latent period for disease expression was also noted, although all disease assessments took place at 7 days after inoculation Seed infection.

A standard technique for assessing seed infection was as follows: Seven hundred and fifty ml of sterilised vermiculite was placed into a 1000 ml volume plastic food container. A plastic template with 20 holes spaced evenly throughout was placed onto the surface of the vermiculite and the seeds to be assessed were sown one per hole in each of the template holes. A further 250 ml of vermiculite was placed over the top of the seed so that the seeds were sown at a depth of between 2 to 4 cm. The seeds were watered after sowing with 125 ml of sterile distilled water. A 500 ml volume plastic food container was inverted over the top of the 1000 ml container and the two containers sealed together using 3 cm width plastic wrap (Glad Wrap®). The assay chamber was then placed in a dark incubator at a temperature of 15° C. for a 7 day incubation period.

After incubation, all the assay chambers were placed in a cool room (4° C.) to stop plant growth prior to assessment. Each assay chamber was then assessed for: seedling emergence, length of the coleoptile for each germinated seed, length of the longest radicle for each germinated seed, total seed germination, and the number of seeds with vegetative stromata produced by *P. semeniperda*. The position of the stromata on the seed was also recorded. A modification of this technique was also used to assay the effects of culture filtrates of *P. semeniperda* on plant development. This technique is hereinafter referred to as the Coleoptile/Radicle length (CR) assay.

(6) Statistical Analyses The computer program Systat (Wilkinson et al., 1992) was used to analyse all the reported data. All experiments were performed at least twice unless otherwise stated. Results from separate trials were pooled when homogeneity of variances was detected using Bartlett's test (Snedecor & Cochran, 1989). Data sets consisting of percentage values were arcsine transformed prior to analysis of variance (Snedecor & Cochran, 1989). Other data sets were transformed to ensure normality of distribution and homogeneity of variance accordingly. Analysis of variance was performed on all data to test for treatment differences. Pairwise comparisons of treatment means were established with Tukey's HSD test (cc=0.05 or 0.01). Experiments which required measurements of the same parameter over time were analysed using univariate repeated measures analysis of variance, and treatment means separated by repeated measures contrasts. Linear or curvilinear functions were fitted to the data, by generating linear or polynomial regression equations. Pairwise comparison of slopes of linear functions was made using t-tests between the various treatments. Experiments were either completely randomized or set up in completely randomized block designs unless otherwise stated.

EXAMPLE 1

Infection of Wheat and *B. Diandrus* by Pyrenophora Semeniperda: The Infection Process Material and Methods Timing of infection sequence.

The timing of the sequence of events leading to infection by *P. semeniperda* (isolate DAR71761) was studied using both light and electron microscopy with seedling and adult leaf pieces of wheat and *B. diandrus*.

Ten day old seedling and adult plants of both wheat and *B. diandrus* were inoculated with a conidial suspension of $1 \times 10^3$ conidia $ml^{-1}$ (surfactants were not used to aid wetting of leaves because they have been reported by Hargreaves, (1982) to induce papillae and halo production in cereal leaves) and immediately placed into a dark dew chamber at $10 \pm 1°$ C., for an incubation period of 3, 6, 9, 12, 15, 18, 21, 24, 36 or 48 h. After the appropriate incubation period, plants were removed from the dew chamber and placed in front of a fan for 10 min to enhance evaporation on the leaves. In the case of seedling plants, leaf pieces (approx. 1.5 cm in length) were excised from the centre of the first true leaf. Adult leaves were sampled by excising leaf pieces (approx. 1.5 cm in length) from the centre of the flag leaf, and each of the next 2 lower leaves. All leaf segments were prepared for examination with the light microscope by using the whole leaf clearing and staining technique of Keane, et al., (1988) or prepared for scanning electron microscopy.

Each experiment consisted of 5 replicates per time period. A replicate was comprised of 5 seedling or 3 adult plants. The experiments were set up in randomised complete block designs within the glasshouse (pre-inoculation) and in the dew chamber (post-inoculation).

For each leaf piece that had been prepared for microscopic examination, the following procedure was undertaken. The leaf piece was mounted in 50% glycerol and examined under 100 to 1000 times magnification with a brightfield light microscope or the leaf piece was examined at 100 to 10000 times magnification using a Jeol JSM-35 scanning electron microscope at the Electron Microscope Unit at the University of New England. The first 20 conidia encountered per leaf piece were counted as either germinated or not. Germination was considered to have occurred if the germ tube was longer than the width of the conidium from which it had arisen. The first 20 conidia per leaf piece which had germinated were examined for the production of infection structures, appressoria and infection hyphae, and the presence or absence of these structures was noted. Due to the nature of scanning electron microscopy only pre-penetration structures of *P. semeniperda* were observed using this technique.

Infection process on floral tissue of wheat.

The infection process of *P. semeniperda* was examined on floral tissue of wheat using light and electron microscopy.

Adult wheat plants were inoculated at anthesis (GS 60) by dipping the inflorescences into a conidial suspension ($1 \times 10^3$ conidia $ml^{-1}$) and placing the plants in a dark dew chamber at $20 \pm 1°$ C. for 24 h. After incubation, the plants were removed from the dew chamber and placed in front of a fan for 10 min to enhance evaporation. Individual florets were then dissected from the inflorescences, and further dissected into groups of: paleas, lemmas, ovaries, and stamens and anthers. Each group was then prepared for light microscopy using the whole leaf clearing and staining technique or electron microscopy.

In another experiment, the plants were placed into the glasshouse after incubation for a further 14 days. Developing caryopses were fixed in 70% ethanol for 48 h, dehydrated through a tertiary butyl alcohol series, and embedded in paraffin. Embedded specimens were softened for 48 h in a 10% glyerol solution with 1% sodium lauryl sulfate (Lawrence, et al., 1981). Serial sections were cut with a rotary microtome at 10 $\mu$m, deparaffinized, and stained with safranin and light green.

In a separate experiment, groups of floral tissue were dissected prior to inoculation. These groups were placed on filter paper moistened with sterile distilled $H_2O$ contained in Petri plates. The floral parts were inoculated by applying a conidial suspension with a handheld atomiser until incipient run-off. The Petri plates were then sealed and incubated in a dark incubator set at $20 \pm 1°$ C. for 24 h. Each group was then prepared for electron microscopy.

Florets were dissected from the same inflorescence. In each experiment, 10 individual florets were dissected from each of 5 replicate plants. Therefore, the floral tissue from a total of 50 florets was examined in each experiment.

The first 20 conidia encountered per floral piece were counted as either germinated or not. Germination was considered to have occurred if the germ tube was longer than the width of the conidium from which it had arisen. The first 20 conidia per leaf piece which had germinated were examined for the production of other prepenetration structures.

Results

Timing of infection sequence.

At 3 h after inoculation, conidia of *P. semeniperda* had germinated to produce two germ tubes with an average length of 16 $\mu$m. The majority of conidia were observed to germinate from both polar cells. Germination from the intermediate cells was rare. Germination from both polar and intermediate cells of the same conidium was never observed. The formation of appressoria was observed at 3 h after inoculation, however, host penetrations were not (Table 2). The proportion of conidia that had germinated was maximal at 12 h and 18 h after inoculation on seedling and adult leaves respectively. This was the case for both wheat and *B. diandrus.* The proportion of conidia that germinated was always lower on adult leaves. In a large majority of cases, germinated conidia produced germ tubes that branched. As a result, large numbers of conidia were observed to have multiple penetration sites associated with a single conidium. In some instances, pieces of hyphae and conidiophores were observed to germinate and produce infection structures.

The proportion of germinated conidia that produced appressoria was maximal at 21 h after inoculation for both species and leaf types. However, five time as many appressoria were produced on the surface of seedling leaves compared to adult leaves. Appressoria were produced on the germ tubes of *P. semeniperda* either: terminally, intercalarially or as hyphopodial-like structures. Appressoria formed terminally on germ tubes, were sharply delimited from the germ tube by a septum. On wheat leaves, appressoria were produced over epidermal cell wall junctions and occasionally, over epidermal cells, stomatal guard cells and trichomes. On leaves of *B. diandrus,* appressoria were produced over stomata and rarely, epidermal cell wall junctions. Appressoria were often associated with the production of extra-cellular sheath-like material.

Sites of attempted penetration by *P. semeniperda* on both wheat and *B. diandrus* were distinguishable by the presence of halos. The halos were easily observed because they were stained differentially and sharply delimited from the uninfected host tissue. Papillae were produced in response to host cell invasion by *P. semeniperda* in both grass species. Papillae began as aggregates of dense cytoplasm and finally appeared as densely stained protrusion beneath appressoria. Papillae were produced adjacent to appressoria on the inner epidermal cell wall surfaces. Infection hyphae of *P. semeniperda* failed to penetrate through this cellular obstruction, and growth of the pathogen ceased.

Approximately ¼ of the sites of attempted penetration were not associated with papillae and the infection hyphae of *P. semeniperda* were able to ramify through the host tissue. Successful penetration of wheat and *B. diandrus* seedling leaves first occurred 12 h after inoculation. Penetration of adult leaves of both species was first observed at 18 h after inoculation. However, successful penetration of seedling and adult leaves of either grass species only occurred in approximately 5 and 1% of germinated conidia respectively. The first infection structure that developed was an intracellular vesicle that formed one or two infection hyphae. Infection hyphae of *P. semeniperda* were not observed to penetrate host cells, but rather grew through the intercellular spaces. Host cells were observed to collapse prior to contact with infection hyphae.

Infection process on floral tissue of wheat.

Conidia of *P. semeniperda* germinated, produced germtubes and subsequent infection structures on all floral tissue tested.

The infection process of *P. semeniperda* on the lemmas and paleas of wheat was similar to that on seedling leaves. That is, germination of a conidium was followed by the production of appressoria and infection hyphae within the intercellular spaces. Cell wall appositions in the form of papillae were also present at some sites of attempted penetration.

Anthers of wheat florets were not observed to become infected by *P. semeniperda.* Rather, infection was limited to the pre-penetration processes. Following germination of conidia, germ tubes grew randomly across the epidermal surface of the anther. Occasionally, a hyphopodium was produced, but penetration of the host tissue was never observed. At 58 h after inoculation, hyphae had grown over a large proportion of the anthers surface.

The infection process of *P. semeniperda* on ovarial tissue of wheat florets was similar to that observed on leaf tissue. Germ tubes and subsequent surface hyphae grew saprophytically on the stigmatic and stylar tissue, but never produced appressoria or other infection structures. Appressoria and hyphopodial-like structures were formed on the cell wall junctions of the ovary. Furthermore, penetration of the ovary wall also occurred without the formation of appressoria. In these cases, germ tubes penetrated the ovary wall without any noticeable swelling, particularly where wounding of the epidermis was apparent.

Infection hyphae of *P. semeniperda* were generally confined to the epidermal and middle layer of the developing caryopsis, where they ramified through the cellular spaces. The integumentary layer was a barrier to growth and hyphae rarely penetrated this band of cells. Hyphae were not observed in the nucellus, micropyle or the embryo sac of the developing seed.

TABLE 2

The time sequence of events during the infection process of *P. semeniperda* on seedling leaves of wheat and *B. diandrus.*

| | Wheat* | | | | | | | | *B. diandrus** | | | | | | | |
|---|---|---|---|---|---|---|---|---|---|---|---|---|---|---|---|---|
| | % Germ | | % App | | % Infect | | % HCN | | % Germ | | % App | | % Infect | | % HCN | |
| Hours | S[a] | A[a] | S | A | S | A | S | A | S | A | S | A | S | A | S | A |
| 3 | 10.5 | 3 | 1 | 0 | 0 | 0 | 0 | 0 | 9.8 | 3.3 | 0 | 0 | 0 | 0 | 0 | 0 |
| 6 | 20.6 | 8.2 | 3 | 0 | 0 | 0 | 0 | 0 | 21.1 | 9.1 | 2.7 | 0 | 0 | 0 | 0 | 0 |
| 9 | 50.1 | 12.9 | 5 | 1 | 0 | 0 | 0 | 0 | 46 | 11 | 4 | 0 | 0 | 0 | 0 | 0 |
| 12 | 99 | 20.7 | 9 | 2.4 | 3 | 0 | 0 | 0 | 98 | 22 | 7.6 | 1.5 | 2.4 | 0 | 0 | 0 |
| 15 | 99 | 21 | 18 | 3 | 4 | 0 | 0.9 | 0 | 99 | 22 | 20.2 | 3.7 | 3.1 | 0 | 0.5 | 0 |
| 18 | 99 | 28 | 21 | 4.0 | 4.3 | 0.6 | 1 | 0 | 99 | 24 | 20.5 | 3.9 | 3 | 0.2 | 0.7 | 0 |
| 21 | 99 | 28 | 22 | 4.2 | 5 | 0.9 | 1.2 | 0 | 99 | 24 | 21.3 | 4.3 | 4.6 | 0.3 | 1 | 0 |
| 24 | 99 | 28 | 22 | 4.2 | 5 | 1.1 | 1.8 | 0.1 | 99 | 24 | 21.3 | 4.3 | 4.6 | 0.9 | 1.5 | 0 |
| 36 | 99 | 28 | 22 | 4.2 | 5 | 1.1 | 1.8 | 0.1 | 99 | 24 | 21.3 | 4.3 | 4.6 | 0.9 | 1.5 | 0 |
| 48 | 99 | 28 | 22 | 4.2 | 5 | 1.1 | 1.8 | 0.1 | 99 | 24 | 21.3 | 4.3 | 4.6 | 0.9 | 1.5 | 0 |

*Germ - is the proportion of conidia that had germinated, App - is the proportion of germinated conidia that had produced appressoria, Infect - is the proportion of germinated conidia that had produced infection hyphae, and HCN - is the proportion of germinated conidia that were associated with host-cell necrosis.
[a]S - is inoculated seedling leaves and A is inoculated adult leaves.

Host-cell necrosis was clearly visible in whole-leaf mounts as collapsed and darkly stained tissue. The proportion of germinated conidia which penetrated the host and that were associated with host-cell necrosis was limited to 1–2% in the seedling leaves of both grass species. Host-cell necrosis in adult leaves of wheat was observed in 0.1% of germinated conidia and none was observed in adult leaves of *B. diandrus.*

Discussion

The infection process of *P. semeniperda* on seedling and adult leaves of wheat and *B. diandrus* and floral tissue of wheat was investigated. Germination of conidia was some 99% on seedling leaves of both species while on adult leaves only 20–30% germinated. This is postulated as a result of the waxy nature of adult leaves. Appressoria were formed as an essential component of the infection process on leaf material and were formed over the aniclinal epidermal cell walls. Ovarial infection was observed to occur either with the formation of an appressorium or through cracks and wounds in the ovary without the formation of appressorium. Papillae were formed within the leaves as a resistance mechanism. The first post-penetration structures formed were intracellular vesicles with infection hyphae which ramified through the intercellular spaces of the mesophyll. Cellular disruption in advance of infection hyphae was observed. This suggested that a toxic metabolite was produced by the pathogen. Infection hyphae formed within the developing caryopsis of wheat grew intercellularly within the confines of the epidermis and the integuments. Infection of the developing embryo was not observed.

The infection process was observed on all tissues tested. This was the first time that a study of this nature had been undertaken with this pathogen. Clearly, *P. semeniperda* was not suited to foliar infection of adult leaves. However, the infection of florets was observed to occur directly through the ovary walls. Thus, increasing the mycoherbicidal potential of *P. semeniperda* as a true seed pathogen. That is, if application of the pathogen can be timed to coincide with anthesis, infection should be established. This may be particularly important when one considers that with the aid of surfactants and other wetting agents the florets of grasses provide an excellent niche for holding water droplets longer than the surfaces of leaves.

Hyphal fragments of *P. semeniperda* were observed to germinate and produce infection structures. This is a particularly important finding because it gives evidence that hyphae of *P. semeniperda* can be used as infective propagules. The use of hyphal fragments of *P. semeniperda* as infective propagules would be attractive because large amount of mycelial inoculum can be produced under liquid shake culture conditions.

The formation of papillae in both wheat and *B. diandrus* leaves was an important resistance mechanism. This should be a consideration when screening potential candidates for inundative control using *P. semeniperda* because those species which do not produce papillae in response to infection may have reduced levels of resistance.

EXAMPLE 2

Infection of Wheat by *Pyrenophora Semeniperda:* Some Factors Influencing Infection Materials and Methods Timing of inflorescence inoculation with respect to growth stage and subsequent seed infection.

Wheat inflorescences were inoculated with *P. semeniperda* (isolate DAR71761) by dipping into a conidial suspension of $5\times10^4$ conidia $ml^{-1}$ at each of four different development stages according to the scale of Zadoks, et al., (1974). Inflorescences were inoculated at: GS 55-half of inflorescence emerged, GS 60-beginning of anthesis, GS 70 end of anthesis with caryopsis water ripe, and GS 75-medium milk development. Plants were incubated with dew at 20° C. for 24 h in the dark immediately after inoculation. Following dew period incubation, the plants were placed back in the glasshouse until seed maturation. Mature seed was assessed for infection by *P. semeniperda.* The experiment consisted of 10 replicates with between 3 and 6 inflorescences per replicate.

Effect of seed inoculation on growth of host plants.

Seeds of wheat and *B. diandrus* were inoculated with *P. semeniperda* (isolate DAR71761) by placing in a conidial suspension of $5\times10^4$ conidia $ml^{-1}$ immediately prior to sowing. After 21 day growth in the glasshouse, the height of the 1st true leaf of *B. diandrus* and the 2nd true leaf of wheat were measured. Furthermore, the dry weight of the whole plants was assessed. The height and dry weight of adult plants was assessed at 8 weeks after inoculation. The experiments were repeated once with 7 replicates. The seedling replicates each had 5 observations.

Timing of inoculation of wheat plants with respect to growth stage and subsequent disease development.

Wheat leaves were inoculated using the cover slip method with 100 $\mu l$ of a conidial suspension ($1\times10^3$ conidia $ml^{-1}$) at each of 4 development stages according to the scale of Zadoks, et al., (1974). The growth stages tested were: GS 13-three leaves unfolded, GS 31-first node detectable, GS 49-first awns visible and GS 60-beginning of anthesis. The 3 uppermost leaves at each growth stage were inoculated and incubated in the dark at 20° C. for 24 h. After incubation the cover slips were removed and plants were placed in the glasshouse. Inoculated leaves were assessed 7 days after inoculation and the data averaged for the 3 leaves. The experiment consisted of 5 replicates per growth stage and was repeated once.

Results

Time of inflorescence inoculation with respect to growth stage and subsequent seed infection.

The infection of mature wheat seeds by *P. semeniperda (isolate DAR*71761) was maximal when inflorescences were inoculated at GS 70 (FIG. 1). However, infection of wheat seeds occurred when inflorescences were inoculated from GS 55 to GS75. The optimal growth stage for infection of wheat seed when calculated from the polynomial regression equation occurs at GS 66±1.4.

Effect of seed inoculation on growth of host plants.

Wheat seeds that had been inoculated with conidia of *P. semeniperda* (isolate DAR71761) at the time of sowing, produced seedlings that were significantly smaller in height and dry biomass at 21 days after inoculation than those that were not inoculated (Table 3) ($P<0.05$). Stromata of *P. semeniperda* were visible on the surface of all inoculated wheat seeds. Seedlings of *B. diandrus* were unaffected by inoculation with conidia of *P. semeniperda* ($P>0.05$). Adult plants of both species at 8 weeks after inoculation were unaffected by inoculation of seeds with *P. semeniperda* ($P>0.1$).

TABLE 3

Effect of seed inoculation by *P. semeniperda* (isolate DAR71761) on shoot growth of wheat and *B. diandrus* seedlings at 21 days after inoculation. Data are means of duplicate experiments each with 7 replicates consisting of 5 observations. Data within the same column followed by a common letter do not differ significantly according to Tukey's HSD test ($P > 0.05$).

| | Wheat | | *B. diandrus* | |
|---|---|---|---|---|
| Treatment* | Shoot height (mm) | Dry weight (g) | Shoot height (mm) | Dry weight (g) |
| Seedling I | 106b | 0.123b | 109 | 0.068 |
| Seedling U | 123a | 0.137a | 112 | 0.067 |

*Seeds were inoculated with conidia of *P. semeniperda* (I) or uninoculated (U)

Timing of inoculation of wheat plants with respect to growth stage and subsequent disease development.

The number or size of lesion formed on wheat leaves was not significantly different when inoculated at GS 13 or GS 31 ($P>0.05$) (Table 4). However, significantly fewer, and smaller lesions were formed when leaves at GS 49 were inoculated ($P<0.05$). No lesions were formed on leaves inoculated at GS 60.

TABLE 4

The effect of plant growth stage on the development of lesions by P. semeniperda (isolate DAR71761) on wheat leaves 7 days after inoculation. Data are means of duplicate experiments each consisting of 5 replicates. Data within the same column followed by a common letter do not differ significantly according to Tukey's HSD test (P > 0.05).

| Growth stage at inoculation | Lesion number[a] | Lesion size* |
|---|---|---|
| 13 | 15.8 + 1.2a | 2.3 + 0.1a |
| 31 | 14.2 + 0.9a | 2.5 + 0.2a |
| 49 | 1.2 + 0.4b | 1 + 0.1b |
| 60 | 0 | 0 |

[a]Data are means of the 3 uppermost leaves inoculated at each growth stage.
*Lesion sizes were based on a 1–4 rating scale as detailed in section 2.5.

Discussion

Infection of wheat seeds occurred at all stages of inflorescence development tested. However, the maximal proportion of seed infection occurred when inflorescences were inoculated at the end of anthesis (GS 70). The optimal growth stage for inoculation of inflorescences calculated from a polynomial regression equation was the middle of anthesis. The inoculation of wheat and B. diandrus seeds prior to sowing did not affect the development of plants after 8 weeks growth. However, seedlings of wheat at 21 days after inoculation were significantly smaller than controls. Wheat leaves were more susceptible to infection by P. semeniperdo at younger growth stages of development. The wheat cultivar used may possess adult plant resistance to infection. The reduction in lesion development on older wheat leaves could be attributed to a decrease in the proportion of germinated conidia and subsequent infection structures.

Although seed inoculation of wheat and B. diandrus did not result in any detrimental effect to overall plant health at adult growth stages, the possibility exists that infection of seedling could reduce the establishment of wheat seedlings. At early stages of crop development this could be a major concern. If seedling establishment of the crop species is harmed, the weed population may receive a significant competitive edge for early soil moisture and nutrients.

Older wheat leaves are more resistant to infection by P. semeniperda. In a field situation with P. semeniperda used as a mycoherbicide, this resistance may be important so that any infection that occurs does not impair crop development. Although adult leaves of B. diandrus were not tested in the studies reported in this Example, conidial germination and subsequent infection structure formation was not markedly reduced.

EXAMPLE 3

The Production of Toxic Metabolites by Pyrenophora Semeniperda In Vitro, and Possible Roles in Pathogenesis Materials and Methods The following method for culture filtrate preparation was used unless otherwise stated. All isolates of *P. semeniperda* and *P. teres* were cultured in the liquid medium of Tomás & Bockus (1987) using the methods described in section (1). Inoculated culture bottles were incubated under laboratory lighting conditions with a temperature range of 17 to 25° C. and shaken on an orbital shaker set at 130 rpm. After 14 days incubation, mycelium was removed by vacuum filtration through Whatman No. 1 filter papers and concentrated under partial vacuum at 75° C. (Buchi Re-121 Rotavapor) to one fifth of the original volume and adjusted to pH 6.5 with 10 N KOH. After refrigeration overnight (4° C.), salts and other precipitates were removed by centrifugation. The culture filtrates were then passed through a sterile 0.45 $\mu$m nitrocellulose filter membrane using a vacuum filtration system. For experiments using bioassay chambers, concentrated culture filtrates were diluted to their original volume with sterile distilled water. Filtrates were stored under refrigeration until use.

One of the following 3 methods was used to assay the effects of culture filtrates on plant development:

1. The coleoptile/radicle (CR) length bioassay described in section (5) was used except that seeds were 'watered' with the culture filtrates prepared in the manner described above. Stromatal formation was not assessed.

2. Preliminary studies of the effects of concentrated culture filtrates on seedling leaves of wheat and *B. diandrus* were undertaken using the leaf infiltration device and method described by Hagborg (1970). However, it was found that infiltration of leaf material using the device was somewhat inconsistent, presumably because of leakage and irregularities in uptake of solutions. A method was devised which overcame these problems while still allowing for a quick turnover of leaf samples. The wetting agent Pulse® was added to the concentrated culture filtrates (0.01% by volume).

Seedling leaves of intact plants were inoculated with a 10$\mu$l drop of culture filtrate dispensed with a micro-pipette. The plant was then placed in a bell jar and a vacuum was applied until the drop of filtrate had infiltrated the leaf. This process usually took about 30 sec. per leaf.

3. For experiments requiring leaves of older plants, a leaf puncture assay was used. The location on the leaf to be inoculated was punctured once with a fine hypodermic syringe. A 10 $\mu$l drop of culture filtrate was then placed on the puncture wound.

In all assays, controls consisted of sterile water and sterile concentrated, uninoculated culture media.

The level of disease that developed on leaves following inoculation with toxic filtrates was assessed visually as described in section (5).

Initial investigations.

To ascertain whether toxic compounds may play a role in the disease caused by *P. semeniperda* initial studies were undertaken using the CR bioassay. For these initial studies, culture filtrates used were not concentrated under partial vacuum and de-salted. Both wheat and *B. diandrus* seeds were 'watered' with filtrates derived from cultures of isolate DAR71761 grown on an orbital shaker or grown in a stationary position. In a separate study, the toxicity of filtrates after heat treatment was tested by comparing culture filtrates that were autoclaved (121° C., 103 kPa) for 15 min and those that were not. Five replicates were used per treatment an the experiments were performed twice.

Toxicity of culture filtrates derived from different isolates of *P. semeniperda*.

Seven isolates of *P. semeniperda* were examined using the CR bioassay to determine whether different levels of filtrate toxicity could be produced by different isolates. The 7 isolates tested were: 580681(DAR71761), 580534, 58020, 580170, 580584, 580129 and 580148. Four replicates were used for each isolate and the experiment was performed twice.

Correlation between disease severity in the glasshouse and reaction to toxic filtrates.

To examine if sensitivity of wheat seedlings to toxic filtrates correlated with susceptibility of wheat seedling to inoculation with conidia, the reactions of wheat seedlings to infiltration with toxic filtrates was compared to the disease severity of wheat seedlings inoculated with the conidia of 5 different isolates. The isolates used in this study were 580681(DAR71761), 580534, 580170, 580520 and 580148. These isolates were chosen because enough conidia were produced by them to carry out the experiments. The reaction of wheat (cv. Cook) seedlings to infiltration with toxic filtrates was evaluated using the vacuum assay method described above. Seedling leaves were inoculated using the cover-slip method with 500 conidia ml$^{-1}$. A low concentration of conidia was used so that disease reactions could be assessed without the confounding effects of lesion coalescence. The level of disease that developed on the wheat seedlings that were inoculated with conidial inoculum was assessed the same way as the toxic reactions. Both filtrate application and conidia inoculation were performed on the same day and plants were returned to the glasshouse and arranged in a randomized block design. Five replicates were used, with each replicate consisting of 5 seedling leaves per pot. Correlations between reaction to toxic filtrates in seedling wheat leaves, disease severity after inoculation with conidia and the results of the CR bioassays were analysed using Pearson's correlation with Bonferroni-adjusted probabilities (Wilkinson, et al., 1992).

Toxin production in relation to filtrate age.

To determine when toxin production was maximal in relation to the age of the culture filtrate, filtrates of isolate DAR71761 were harvested after different lengths of incubation. The first harvest occurred after 6 days and thence every 3 for a total of 30 days. At each harvest, the pH of the filtrate was evaluated and the dry weight of the mycelium produced was ascertained. The CR bioassay with wheat and *B. diandrus* seeds was set up using sterile, concentrated and re-diluted filtrates. The experiment consisted of 4 replicates and was repeated once. The correlations between filtrate pH, mycelia dry weight and coleoptile length were analysed using the methods described above.

Relationship between filtrate toxicity and pH.

The results from the above experiments suggested that the pH of culture filtrates reduced markedly over time. It is possible that the toxic factor may be pH related. Therefore, to ascertain whether the toxicity in filtrates was related to pH, the pH of inoculated and uninoculated filtrates were adjusted correspondingly. Cultures of isolate DAR71761 were grown for 12 days and harvested. The pH of both inoculated and uninoculated bulked filtrates (after concentration and dilution) were measured and gave readings of pH 5.0 for inoculated filtrates and pH 6.5 for uninoculated filtrates. Treatments were prepared by removing half of each filtrate type and adjusting the pH using 10 N KOH and 2 N HCl so that the following treatments were tested using the CR bioassay with wheat:
(i) inoculated filtrate pH 5.0,
(ii) inoculated filtrate pH 6.5,
(iii) uninoculated filtrate pH 5.0,
(iv) uninoculated filtrate pH 6.5, and
(v) sterile distilled water.
Treatments had 5 replicates and the experiment was not repeated.

Effect off filtrate concentration on toxic reaction type

Five dilutions of concentrated culture filtrates were tested for their effect on reaction type in infiltrated wheat and *B. diandrus* seedling leaves. Sterile culture filtrates of isolate 580170 that were concentrated to ⅕ of their original volume were denoted as 1× stock filtrates. From these stock filtrates, dilutions were made resulting in ⅕×, ⅒×, 1/100×, and 1/1000× the concentration of the 1× stock filtrates. The same dilutions were made for uninoculated culture filtrates. Five replicates (each consisting of 5 seedling plants) were used for each treatment and the experiment was repeated once. Filtrates were applied using the vacuum assay method.

Effect of toxic filtrates at different plantgrowth stages

The effect of toxic culture filtrates on plants at different developmental stages was assessed using the leaf puncture assay. Concentrated culture filtrates of isolate 580170 were applied to sheat plants at 4 different growth stages according to the decimal code for cereal growth stages (Zadoks,et al., 1974): seedling (GS 13), 1st node detectable (GS 31), first awns visible (GS 49) and beginning of anthesis (GS 60). Plants received filtrate applications when they had grown to the stages tested. The 3 top leaves at the growth stage were inoculated at each of 3 leaf positions: base, middle and tip. For each treatment there were 10 replicate plants. The treatments were all sown simultaneously. Filtrate application and disease assessments occurred over several months. The experiment was repeated once with 5 replicates in the second experiment.

Host specificity of culture filtrates

The host specificity of culture filtrates was evaluated by applying filtrates of isolate 580170 to the leaves of several plant species using the vacuum infiltration assay. Plants of the following species were tested: wheat, *B. diandrus, Lablab purpureus* (L.) Sweet, *Gossypium hisutum L., Helianthus annuas L., Xanthium occidentale* (Noogoora burr). Prior to sowing, *X. occidentale* fruits were cut at the distal end of speed up seed germination. Seeds of the species tested were sown into vermiculite contained in seeding trays. After 7 days growth, seedlings were transplanted into polystyrene cups one per cup. After a further 7 days, the first true leaves of all species were inoculated. Ten replicates were used for each treatment and the experiment was repeated once.

A comparison of toxic filtrates produced by *P. semeniperda* and *P. teres*

A comparison of the culture filtrates of both *P. semeniperda* and *P. teres* was made using the CR bioassay technique. This was done because *P. teres* is not regarded to be a pathogen of wheat, but is considered to be a pathogen of Bromus spp. (Sivanesan, 1987). This experiment was initiated to determine whether culture filtrates of a pathogen of *B. diandrus* which is known to produce toxins (i.e. *P. teres*) could be more toxic to *B. diandrus* and less toxic to wheat than filtrates of *P. semeniperda,* produced under the same cultural conditions.

Cultures of isolates DAR71761 and 580170 of *P. semeniperda,* and isolates WI1535 and WI8712 of *P. teres* were established. Five replicates of each treatment were used and the experiment was repeated once.

Results

In none of the experiments was germination affected by culture filtrates when compared to controls.

Initial investigations

Culture filtrates of *P. semeniperda* (isolate DAR71761) had a marked negative effect on length of both coleoptiles and radicles of wheat and *B. diandrus* (Table 5). Culture filtrates that were produced whilst being incubated on a rotary shaker were significantly more toxic to coleoptiles and radicles of wheat and coleoptiles of *B. diandrus* than filtrates produced whilst unshaken (P<0.05). Filtrates whether inoculated or not, significantly reduced radicle lengths of both wheat and *B. diandrus* when compared to application of water (P<0.05). Filtrates were consistently more toxic to wheat than *B. diandrus.*

TABLE 5

The effect of culture filtrates of *P. semeniperda* (isolate DAR71761) produced either whilst being incubated on a rotary shaker or unshaken, on coleoptile and radicle lengths of wheat and *B. diandrus* after 7 days growth in a CR bioassay chamber. Data are means of duplicate experiments. Data within the same column followed by a common letter are not significantly different according to Tukey's HSD test (P > 0.05).

|  | Wheat | | *B. diandrus* | |
| --- | --- | --- | --- | --- |
| Treatment* | Coleoptile length (mm) | Radicle length (mm) | Coleoptile length (mm) | Radicle length (mm) |
| Shaken I | 23a | 35a | 71a | 89a |
| Unshaken I | 100bc | 122c | 84b | 92e |
| Shaken U | 103c | 118c | 91c | 91a |
| Unshaken U | 94b | 98b | 86b | 88a |
| Water | 103c | 150d | 87b | 101b |

*Treatments are either inoculated culture filtrates (I) or uninoculated culture filtrates (U).

Autoclaving had no effect on the toxicity of filtrates. Filtrates remained equally toxic to coleoptiles and radicles of both wheat and *B. diandrus* whether they were autoclaved or not. Uninoculated filtrates significantly reduced the length of wheat coleoptiles and radicles and *B. diandrus* radicles when compared to application of water (P<0.05).

Toxicity of culture filtrates derived from different isolates of *P. semeniperda*

Culture filtrates of isolate 580170 reduced coleoptile and radicle lengths of both wheat and *B. diandrus* more than any other isolate. Culture filtrates from 3 isolates (580170, DAR71761, 580148) reduced coleoptile lengths of wheat seedlings by more than 50% compared to the controls and were not significantly different from each other (P>0.05). Only culture filtrates from isolates 580170 and DAR71761 were able to reduce coleoptile lengths of *B. diandrus* by more than 40%. However, filtrates from isolate 580170 were able to reduce cleoptile and radicle lengths of wheat and *B. diandrus* by more than 50%. Filtrates from isolates 580584 and 580520 did not reduce coleoptile lengths of wheat when compared to the controls (P>0.05). In addition, filtrates from isolate 580520 did not reduce coleoptile lengths of *B. diandrus* relative to controls (P>0.05). Application of uninoculated filtrates did not significantly reduce coleoptile lengths of wheat or *B. diandrus* (P>0.05) compared to water.

TABLE 6

Toxicity of culture filtrates produced by 7 different isolates of *P. semeniperda* on coleoptile and radicle lengths of wheat and *B. diandrus* after 7 days growth in a CR bioassay chamber. Data are means of duplicate experiments. Data within the same column followed by a common letter are not significantly different according to Tukey's HSD test (P > 0.05).

|  | Wheat | | *B. diandrus* | |
| --- | --- | --- | --- | --- |
| Isolate | Coleoptile length (mm) | Radicle length (mm) | Coleoptile length (mm) | Radicle length (mm) |
| Water | 56d | 104d | 71a | 80d |
| Uninoculated | 55d | 73cd | 75a | 61c |
| 580170 | 13a | 18a | 18a | 33a |
| 580681 | 24ab | 34b | 44b | 44b |
| 580129 | 41c | 51c | 60c | 58c |
| 580148 | 20a | 35b | 65cd | 61c |
| 580584 | 50d | 59c | 67d | 58c |
| 580534 | 31b | 34b | 67d | 54c |
| 580520 | 45cd | 54c | 74a | 61c |

*580681 is the isolate DAR71761

Figure 2:
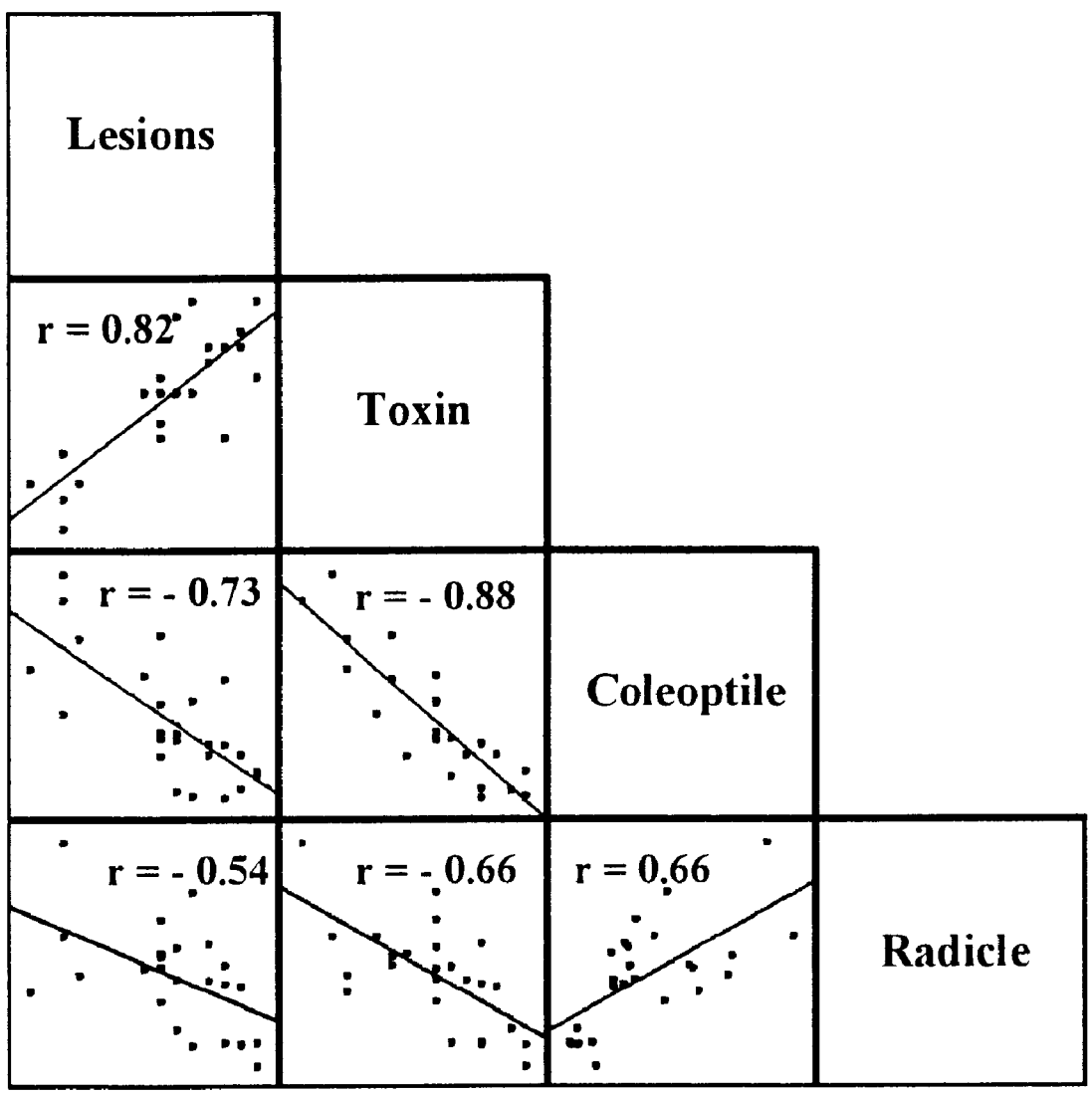
FIG. 2: Provides a scatterplot matrix of correlations between disease severity (lesions) in the glasshouse, reaction to toxic filtrates (toxin), coleoptile length and radicle length of seedling wheat plants at 7 days after inoculation with either conidia or toxic filtrates of P. semeniperda. All correlations (r-values) were significant at P<0.01, except for the correlation between lesions and radicle (P<0.05), according to Pearson's correlation with Bonferroni adjusted probabilities. The experiment was repeated with similar results.
Figure 3A:
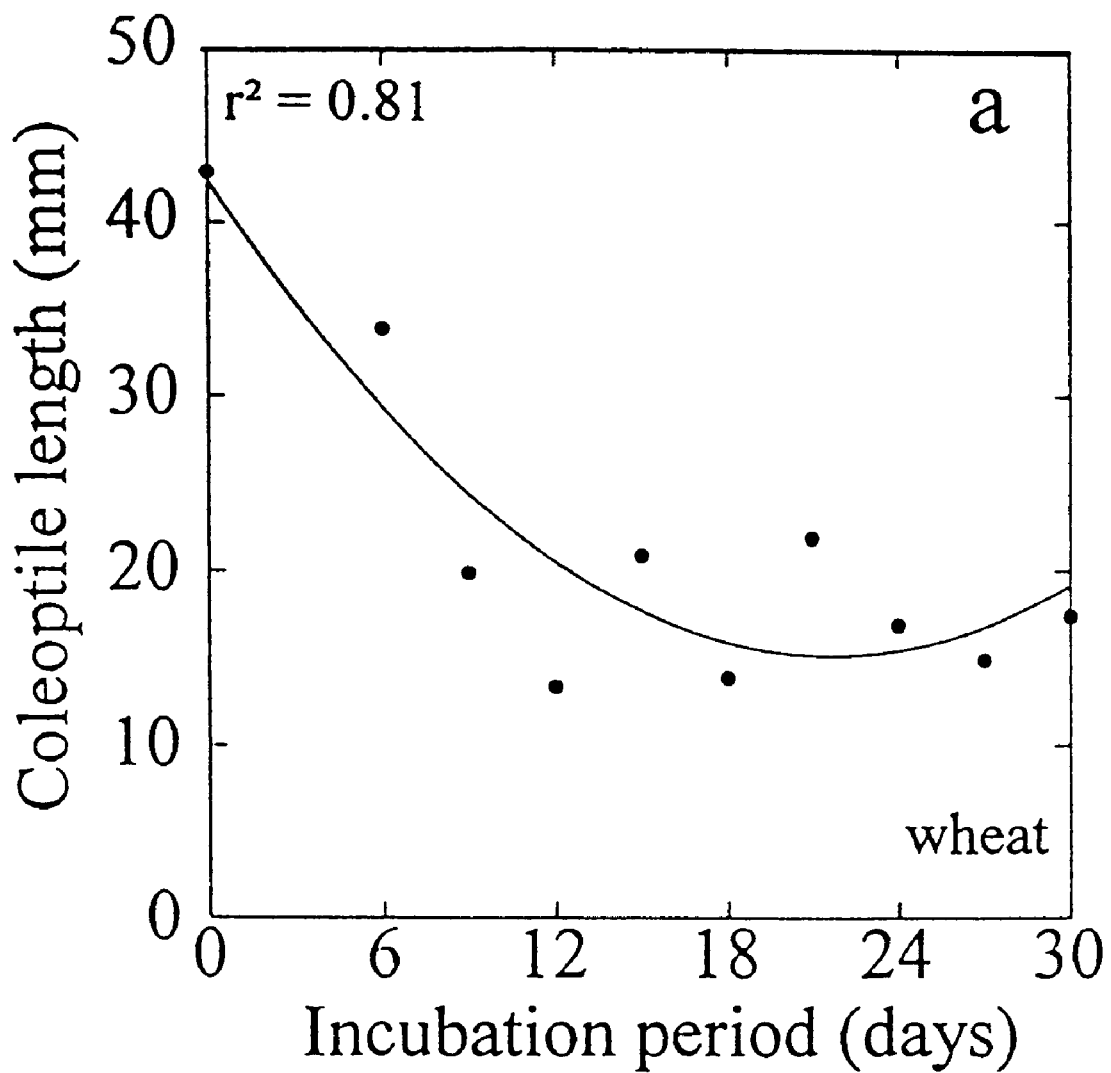
FIGS. 3a–3d: Show the effect of toxic culture filtrates of P. semeniperda (isolate 580170) harvested at different days after culture inoculation on the length of wheat and B. diandrus coleoptiles and radicles after 7 days growth in a CR bioassay chamber. Data are means of 5 replicates each with 20 observations. a) The regression equation is $Y=42.4 (\pm4.2)-2.5(\pm0.6)X+0.06(\pm0.02)X^2$, c) the regression equation is $Y=60.9(\pm7.6)-2.7(\pm1.1)X+0.06(\pm0.03)X^2$ where Y=coleoptile length of seedlings at 7 days after application of toxic filtrate and X=harvest time (days) of filtrates after inoculation, d) the regression equation is $Y=56.4(\pm4.2)-0.87(\pm0.23)X$ where Y=radicle length of seedlings at 7 days after application of toxic filtrate and X=harvest time (days) of filtrates after inoculation.
Figure 3B:
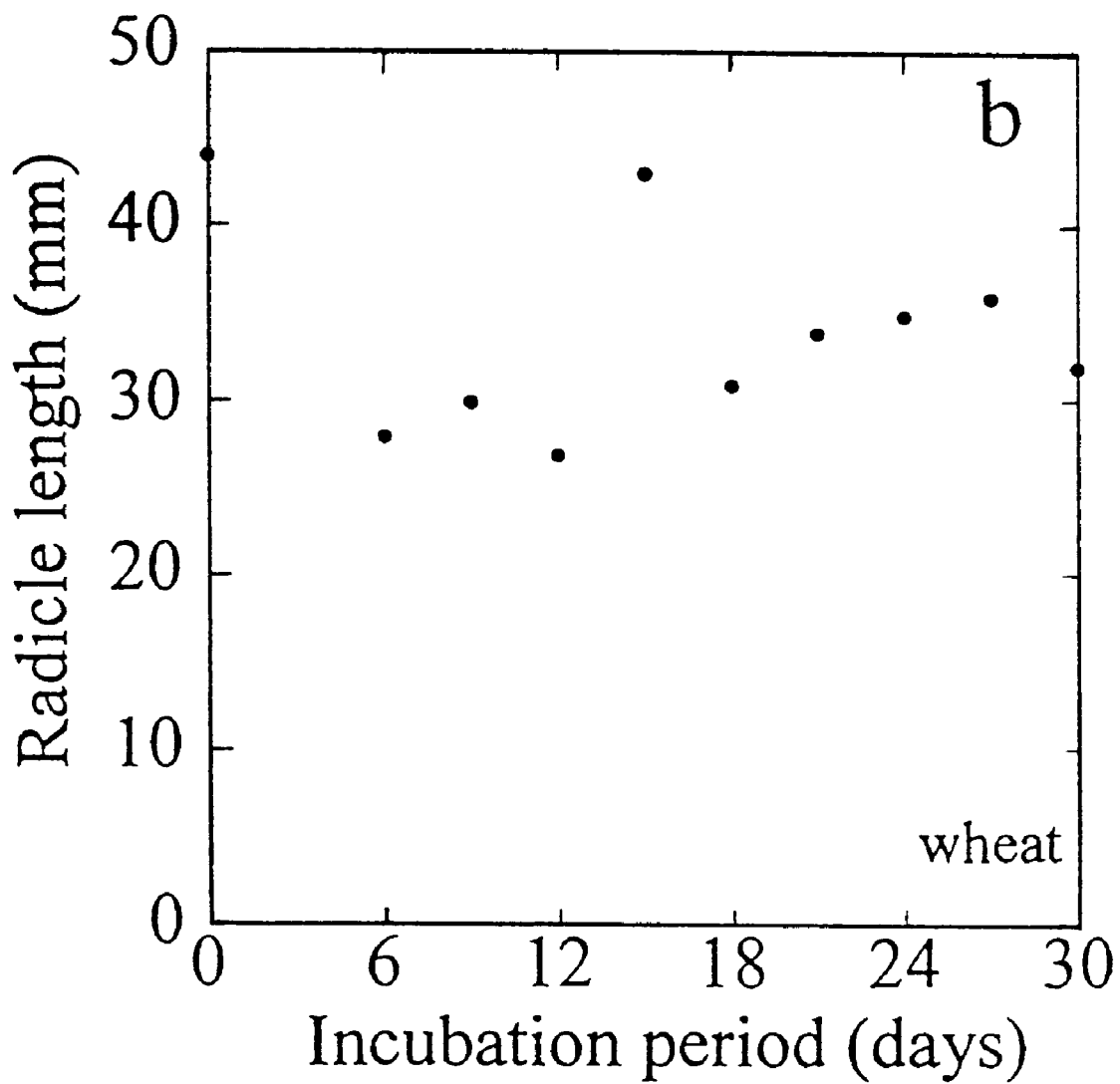
Figure 3C:
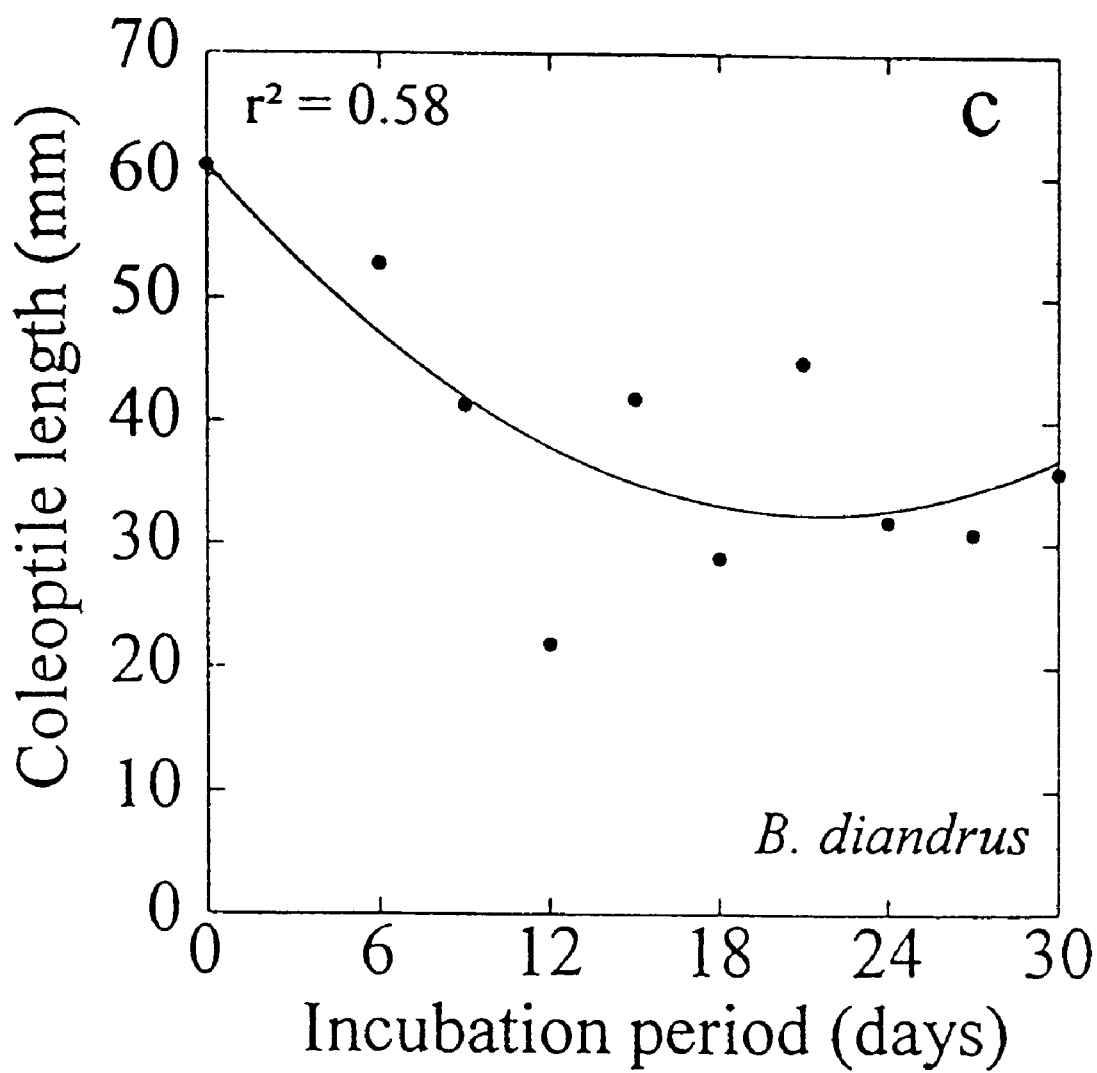
Figure 3D:
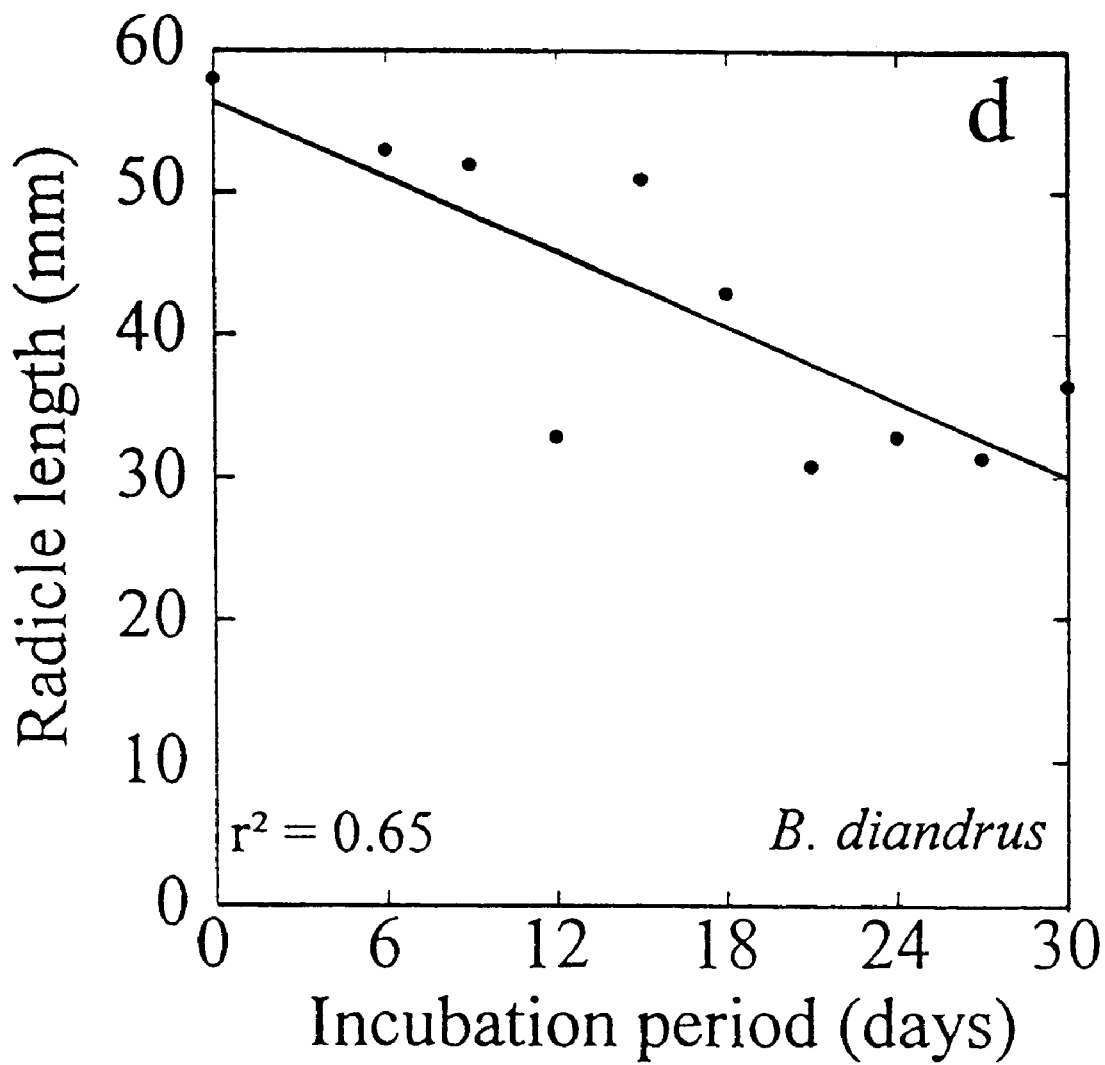

Correlation between disease severity in the glass house and reaction to toxic filtrates The symptoms of toxic infiltration into wheat leaves were very similar to those formed after infection with conidial inoculum. Chlorotic halos and necrotic tissue were the primary symptoms. The level of disease severity that developed in seedling wheat plants inoculated with conidia of *P. semeniperda* was closely correlated with the reaction of seedling wheat plants to infiltration with toxic culture filtrates (Table 7, FIG. 2). Disease severity and reaction to toxic filtrate was highest when plants were inoculated with conidia and toxic filtrates of isolates DAR71761 and 580170 (P<0.05). Significantly less severe disease and lower toxic reaction was observed when wheat seedlings were inoculated with conidia or filtrates of isolate 580520. A significant correlation was observed between disease severity (from conidial inoculation) and reaction to toxic filtrates after 7 days (P<0.01). A significant negative correlation was observed between the coleoptile lengths of wheat seedlings after toxic filtrate application and growth in a CR bioassay chamber for 7 days and reaction to toxic filtrates in wheat seedling leaves after 7 days (P<0.01). Similarly, a significant negative correlation was observed between disease severity and coleoptile lengths of wheat seedlings after toxic filtrate application and growth in a CR bioassay chamber for 7 days (P<0.01). Correlations of lower magnitude were observed between wheat radicle length after filtrate application and growth in a CR bioassay chamber for 7 days and disease severity, reaction to toxic filtrates and coleoptile length.

TABLE 7

Glasshouse disease severity and reactions of wheat to toxic filtrates produced by 5 isolates of *P. semeniperda*. Data are means of duplicate experiments. Data in the same column followed by a common letter are not significantly different according to Tukey's HSD test (P > 0.05).

| Isolate | Glasshouse disease severity | Reaction to toxic filtrate |
| --- | --- | --- |
| 580681 (DAR71761) | 3.6a | 3.5a |
| 580170 | 3.5ab | 3.9a |
| 580534 | 3.0b | 2.8b |
| 580520 | 1.6c | 1.7c |
| 580148 | 2.9b | 3.0b |

Toxin production in relation to filtrate age

The pH of filtrates dropped markedly over the duration of the experiments. The pH of inoculated filtrates fell from pH 6.5 at day 6 to pH 4.0 at day 30. The pH of uninoculated filtrates dropped from pH 6.5 at day 6 to pH 6.0 at day 30. Mycelial dry weight increased from 0.055 g at day 6 to 0.516 g at day 30. After 6 days incubation, coleoptile lengths of wheat and *B. diandrus* were reduced by 26 and 17% respectively compared to controls. The effects of toxic filtrates (FIG. 3) on coleoptile lengths of wheat and *B. diandrus* were maximal when filtrates which had been incubated for 12 days were applied. The effects of filtrate age on coleoptile lengths of both wheat and *B. diandrus* followed an inverse logistic growth law (Snedecor & Cochran, 1989). The effects of toxic filtrates on radicle growth of both wheat and *B. diandrus* did not change markedly with the length of culture filtrate incubation, although a downward trend was observed for the effect on *B. diandrus* radicles. The regression lines in FIG. 3, (b and d) were not significantly different than a horizontal line (P>0.05).

Figure 4:
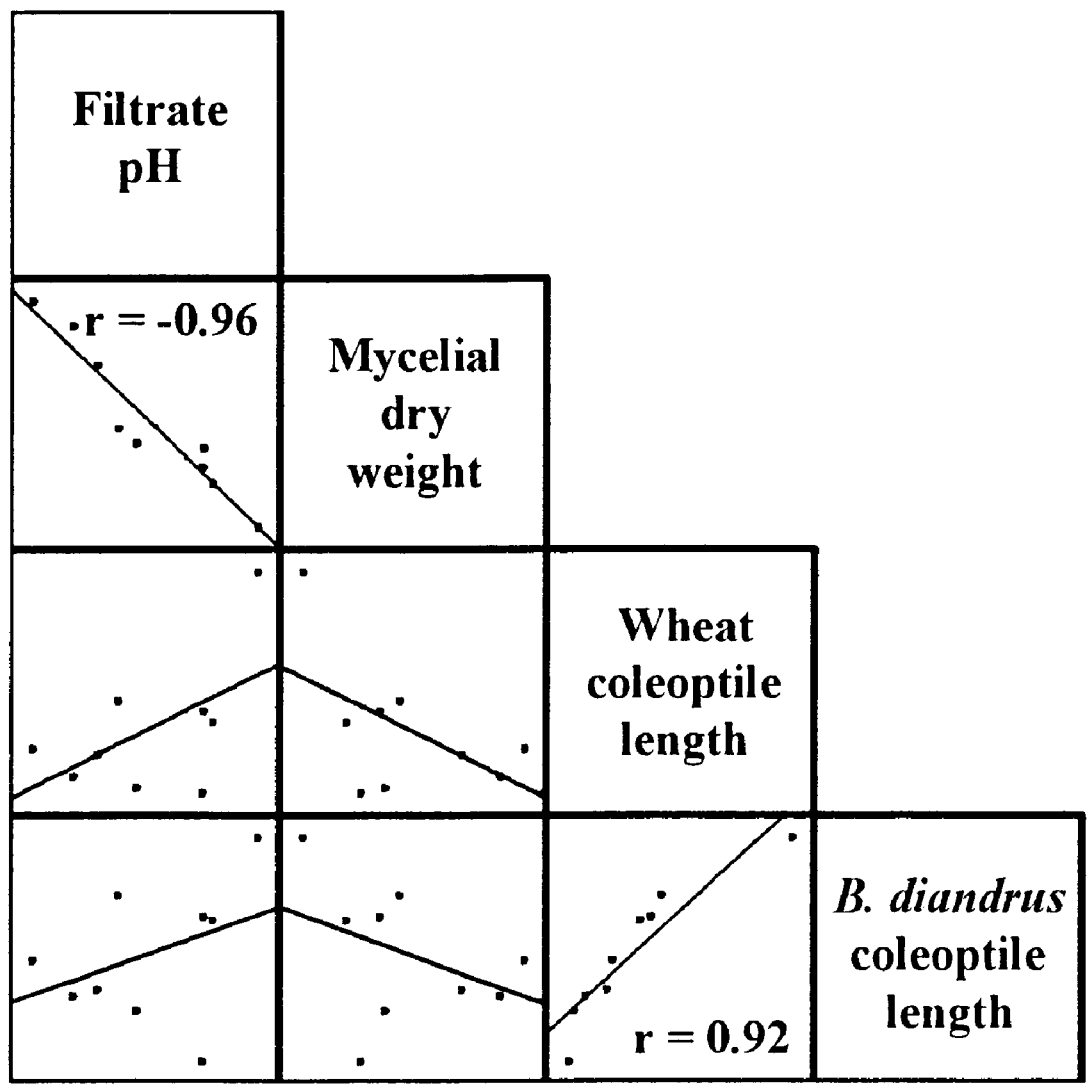
FIG. 4: Provides scatterplot matrix of correlations between toxic filtrate pH, mycelial dry weight and coleoptile length of seedling wheat and B. diandrus plants and 7 days after filtrate application. Correlations with r-values were significant at P<0.01.

A significant negative correlation was observed between filtrate pH and mycelial dry weight (P<0.01) (FIG. 4). A positive correlation was observed between coleoptile lengths of wheat and *B. diandrus* (P<0.01). No significant correlations were observed between filtrate pH and mycelial dry weight and wheat or *B. diandrus* coleoptile length.

Relationship between filtrate toxicity and pH

Amending the pH of culture filtrates did not affect the toxicity of filtrates. The effect of inoculated filtrates on coleoptile and radicle length of wheat plants remained similar irrespective of filtrate pH (P<0.01). Similarly, the effect of uninoculated filtrates on coleoptile and radicle length of wheat plants was statistically similar irrespective of filtrate pH (P<0.01).

Effect of filtrate concentration on toxic reaction type

The most severe reaction types occurred on both wheat and *B. diandrus* after application of undiulted filtrates of *P. semeniperda* (isolate 580170) (Table 8). Latent period for symtom expression varied from <12 h to 7 days. Latent period was shorter in infiltrated wheat leaves than *B. diandrus* leaves infiltrated with the corresponding filtrate concentration. Similarly, reaction type in *B. diandrus* leaves was lower than that of the corresponding filtrate concentration in wheat leaves. Symptoms were observed in wheat leaves infiltrated with filtrates of 1/100 concentration. Symptoms were not observed in either wheat or *B. diandrus* leaves infiltrated with filtrates at 1/1000 concentration. Slight chlorosis was observed in some wheat seedlings infiltrated with 1× uninoculated filtrates. Otherwise, controls of different concentrations of uninoculated culture filtrates and sterile water resulted in no reactions when infiltrated into wheat and *B. diandrus* seedling leaves.

TABLE 8

The latent period and reaction type of wheat and *B. diandrus* seedling leaves to different concentrations of toxic filtrates of *P. semeniperda* (isolate 580170) 7 days after infiltration. Data are means of duplicate experiments consisting of 5 replicates each of 5 observations. Data within the same column followed by a common letter are not significantly different according to Tukey's HSD test (P > 0.05).

| | Wheat | | *B. diandrus* | |
|---|---|---|---|---|
| Filtrate concentration | Latent period | Reaction type | Latent period | Reaction type |
| 1 | <12 h | 4.5a | >72 h | 3a |
| 1/5 | >72 h | 3.8ab | 7 days | 1.5b |
| 1/10 | 5 days | 3.0b | NR | 1 |
| 1/100 | 7 days | 2.2c | NR | 1 |
| 1/1000 | NR | 1 | NR | 1 |

NR = No symptoms observed at 7 days after filtrate application.

Effect of toxic filtrates at different plant growth stages

Reaction types of wheat plants infiltrated with toxic culture filtrates were higher when applied to plants at the 3-leaf seedling stage (GS13) or when the first node was detectable (GS31) than when plants were infiltrated when the first awns were visible (GS49) or at anthesis (GS60) (P<0.05) (Table 9). The period for symptom expression was shorter at earlier growth stages. Lesions were generally bigger when plants were infiltrated at earlier growth stages.

TABLE 9

The reaction of wheat leaves infiltrated with toxic filtrates of *P. semeniperda* (isolate 580170) at 4 different growth stages (according to the scale of Zadoks, et al., 1974). Data are means of 10 replicates, each consisting of 9 observations. Data followed by a common letter are not significantly different according to Tukey's HSD test (P > 0.05). The experiment was repeated with similar results.

| Growth stage | Latent period | Reaction type |
|---|---|---|
| 13 | <12 h | 4.2a |
| 31 | <12 h | 4.0a |
| 49 | 48 h | 3.2b |
| 60 | 36 h | 3.3b |

Host specificity of culture filtrates

Symptoms on leaves of wheat and *B. diandrus* were observed when leaves were infiltrated with culture filtrates. No symptoms were observed on leaves of *L. purpureus, G. hirsutum, H. annuas,* or *X. occidentale* after infiltration with culture filtrates. Occasionally, slight chlorosis was observed in plants which were infiltrated with uninoculated filtrates.

A comparison of toxic filtrates produced by *P. semeniperda* and *P. teres*

Culture filtrates of both isolates of *P. semeniperda* (580170 and DAR71761) significantly reduced the length of wheat coleoptiles and radicles after 7 days growth in a CR bioassay chamber (P<0.05) (Table 10). Isolates of *P. teres* (WI1535 and WI8712) did not reduce the length of wheat coleoptiles or radicles when compared to uninoculated filtrates (P>0.05). *P. semeniperda* and *P. teres* isolates reduced length of *B. diandrus* coleoptiles and radicles significantly when compared to uninoculated filtrates and water (P<0.05). *P. teres* (isolate WI8712) reduced coleoptile length of *B. diandrus* by 33%.

TABLE 10

The effect of culture filtrates of *P. semeniperda* (isolates 580170 and DAR71761) and *P. teres* (isolates WI 1535 and WI 8712) on coleoptile and radicle lengths of wheat and *B. diandrus* after 7 days growth in a CR bioassay chamber. Data are means of duplicate experiments each consisting of 4 replicates with 20 observations. Data within the same column followed by a common letter are not significantly different according to Tukey's HSD test (P > 0.05).

| | Wheat | | *B. diandrus* | |
|---|---|---|---|---|
| Treatment | Coleoptile length (mm) | Radicle length (mm) | Coleoptile length (mm) | Radicle length (mm) |
| 580170 | 14a | 29a | 17a | 32a |
| *580681 | 39b | 46b | 51b | 57b |
| WI 1535 | 60c | 74c | 57b | 53b |
| WI 8712 | 64c | 79c | 49b | 51b |
| Uninoculated | 60c | 61bc | 74c | 69bc |
| Water | 60c | 107d | 73c | 84c |

*580681 is the isolate DAR71761

Discussion

*P. semeniperda* was shown to produce toxic metabolites under in vitro conditions. The toxin/s are heat stable and only produced when cultures are agitated. Using a bioassay which used coleoptile and radicle length after application of toxic filtrates, it was shown that filtrates of *P. semeniperda* cultures had a severe impact on seedling growth of both wheat and *B. daindrus*. Furthermore, infiltration of wheat and *B. daindrus* leaves with toxic filtrates produced symptoms similar to those produced by conidial inoculation. The relative toxicity of filtrates derived from several *P. semeniperda* isolates and infiltrated into wheat leaves was highly correlated with the relative infectivity of conidia produced by these isolates. Toxicity of filtrates was not related to culture pH or mycelial growth. Culture filtrates were toxic to wheat and *B. diandrus* as soon as 6 days after culture inoculation and was maximal at 12 days. Incubation for a further 18 days did not result in greater toxicity of culture filtrates. Culture filtrates which had been diluted to 1/100 were capable of producing symptoms in wheat seedlings. However, only filtrates with greater than 1/5 concentration were able to produce symptoms on *B. diandrus* seedling leaves. Toxicity of filtrates was related to plant age. Plants older than GS31 were significantly less susceptible to the toxic filtrates. A degree of host specificity was observed. Toxic filtrates infiltrated into leaves of wheat *B. diandrus, L. purpureus, G. hisutum, H. annuus,* and *X. occidentale* produced characteristic symptoms only on wheat and *B. diandrus*. A comparison of the toxicity of *P. semeniperda* and *P. teres* grown under the same cultural conditions was made. *P. teres* did not affect wheat coleoptile growth, but effected the coleoptile growth of *B. diandrus*. In all cases, filtrates produced by *P. semeniperda* had a greater effect.

EXAMPLE 4

Field Evaluation

Materials and Methods

Field trials were conducted in Armidale and Orange NSW. The details of the sites are as follows:

1. Armidale address: University of New England's farm "Laureldale", Clark's Road Sail: Basaltic black earth Average annual rainfall: 780 mm Previous land use: various crop trials.

This plot was sprayed with glyphosate (Roundup CT®) and rotary hoed.

2. Orange

Address: agricultural Research and Veterinary Centre, Forest Road

Soil: Basaltic, red soil

Average annual rainfall: 840 mm

Previous land use: Pasture trails

This plot was sprayed with paraquat and diquat and rotary hoed.

In all field trials, seedlings were produced as described insection (2). When plants were 14 days old, they were removed from the glasshouse and 'hardened off' for 7 days under field conditions prior to transplanting. In all trials except the one conducted in 1992/93, the plants were transplanted into depressions made in the earth with a planting board. The planting board measured 1 m×1 m and had wooden spikes spaced 10 cm from each other, such that the spikes made rows of 10×10. When the spikes were forced into the ground, 100 depression were made allowing for easy planting of seedlings. After transplanting, seedlings were watered immediately. The trials were irrigated when insufficient rainfall fell for good crop development. Weeds in plots were controlled manually by chipping and the interplot spaced were controlled by mowing.

Seeds harvested from field trials were threshed, and chaff removed prior to assessment using the CR bioassay outlined in section (5).

Preliminary field studies 1992/93 Season

Seedlings of *B. diandrus* and wheat were transplanted in a split-plot design with four replicates. Each sub-plot consisted of eight rows (5.5 m long) spaced 20 cm apart. Plants were spaced 18 cm apart. Therefore, 250 plants were grown per sub-plot. Fifty cm interplot spaces were maintained.

Two treatments were used, uninoculated plots (sprayed with sterile water on inoculation nights) and inoculated plots (sprayed with a conidial suspension of $55 \times 10^3$ conidia $ml^{-1}$).

Wheat and *B. diandrus* were inoculated separately when 50% of the population has reached anthesis (GS 60, Zadoks, et al., 1974). Wheat was inoculated once on the night of Nov. 10, 1992 using a hand held atomiser. *B. diandrus* was inoculated four times with the first inoculation occurring on the Nov. 16, 1992 and for three weeks thereafter.

Seeds were harvested at maturity by hand. For each sub-plot the inner 6 rows (each of 4 m length) were harvested. For sub-plots containing *B. diandrus,* every 2nd inflorescence was harvested so that a second harvest could be taken a month after the first.

Seed collected at the first harvest was placed under conditions of high humidity, using the following technique: A saturated solution of $K_2SO_4$ was prepared. One hundred ml of this solution was placed into a plastic container (750 ml volume, 12×17×6 cm). Several wire racks were constructed from nylon covered fly-screen mesh (14×9×3 cm high). A rack was placed into the solution and 100 seeds were placed on it. A lid was put on the container and Parafilm® was used to seal it. Each container was placed in an incubator at 20±1° C. for one month. After the one month period the seeds were removed and a CR bioassay was carried out.

After the second harvest, 10 individual inflorescences were removed at radom from each of the four replicates. The seeds from individual florets of each inflorescence were examined for stromatal development of *P. semeniperda* and its position on the inflorescence was noted on a schematic inflorescence map.

Trials of different inoculum types

Two similar trials were planted in 1993/94 and 1994/95. Seedlings were transplanted into plots arranged in a completely randomized block design with 4 replicates. Each plot consisted of 100 plants in 10 rows spaced 10 cm apart. In these trials, mixed populations of *B. diandrus* and wheat were grown. Each row was planted such that it consisted of alternating wheat and *B. diandrus*.

The following treatments were tested:

1. Sprayed with mycelium suspended in a 2% sucrose solution (four times). Mycelium was prepared by growing in the liquid medium of Thomas and Bockus (1987) for 14 days. Mycelium was harvested and the medium filtered out through Whatman No. 1 filter paper in a Buchner funnel. The mycelium was weighed and 25 g was comminuted in a blender in 200 ml of sterile water for 2.5 min. Water was added to make up 1 . Two % sucrose was added.

2. Sprayed with mycelium suspended in water(four times, 1993/94only).

3. Mycelium encased in an alginate pellet applied 3 weeks prior to anthesis (1993/94 only). The method of Walker & Connick (1983) was used with the incorporation of kaolin clay into the liquid phase.

4. Spraying with conidial suspension at anthesis ($45 \times 10^3$ conidia $ml^{-1}$).

5. As for 4 but also one week after anthesis.

6. As for 4 but also for two consecutive weeks after anthesis.

7. As for 4 but also for three consecutive weeks after anthesis.

8. Sprayed with conidia suspended in 'toxin' culture filtrate (1994/95).

9. Sprayed with 'toxin' culture filtrate only (1994/95 only).

10. Sprayed with sterile distilled water.

All inoculations were started when *B. diandrus* was reached anthesis, NOT wheat, and each plot received 250 ml of inoculum suspension.

Each plot was harvested at maturity. The innermost 64 plants were harvested.

Inoculation of six grass species

Seedlings were transplanted into the field plots in Orange in a completely randomised spit-plot block design with 4 replicates. Main-plots were either inoculated or not and sub-plots consisted of the following different grass species: *Triticum aestivum* (wheat); *Avena futa* (wild oats); *Bromus diandrus* (bromegrass); *Lolium rigidum* (annual ryegrass); *Hordeum leporinum* (barley grass) and *Vulpia bromoides* (vulpia). Sub-plots consisted of six rows of six seedlings spaced 20 cm apart. An inter-plot spacing of 0.6 m was used.

Plots were inoculated with conidia suspended in water ($3.2 \times 10^4$ condia $ml^{-1}$) when the species had reached anthesis. Each replicate was sprayed four times with 250 ml of inoculum. After the first inoculation (Nov. 13, 1993) a storm hit the plots so another inoculation was carried out on the night of the Nov. 14, 1993. The following two inoculations were all spaced one week apart.

The inner 16 plants of each species were harvested at maturity. Seeds of *A. fatua* were harvested on different dates because the seed of this species fell to the ground on maturity.

Results

Preliminary field trial 1992/93 Season

January 1993 harvest. Infection of wheat and *B. diandrus* seeds by *P. semeniperda* resulted in a significantly smaller proportion of seeds germinating and emerging (Table 11). The coleoptile lengths seedlings derived from inoculated seeds were also reduced compared to the uninoculated controls. The proportion of wheat and *B. diandrus* caryopes which showed stromatal development by *P. semeniperda* was relatively low (14 and 12% respectively). *B. diandrus* seeds with stromata of *P. semeniperda* never germinated. *P. semeniperda* has a significantly (P<0.05) greater detrimental effect on wheat than *B. diandrus* when measured as a reduction in emergence. However, the effect on coleoptile lengths when calculated as a percentage reduction compared to the uninoculated controls (25%, wheat and 18%, *B. diandrus*) was not significantly different (P>0.05).

TABLE 11

The effect of inoculation of field wheat and *B. Diandrus* with *P. semeniperda* on caryopses germination and development, when caryopses were harvested in January 1993. Significant differences (P > 0.05) were observed between uninoculated (U) and inoculated (I) caryopses in all parameters tested. Data followed by a different letter in the same column were significantly different (P > 0.05). Data are means of 4 replicates and duplicate CR bioassays.

| Species | % Germ | | % Emerge | | Col length (mm) | | Germinated Seeds with stroma[a] | | Ungerminated Seeds with stroma[b] | |
|---|---|---|---|---|---|---|---|---|---|---|
| | U | I | U | I | U | I | U | I | U | I |
| B. diondrus | 98 | 88 | 93 | 47a | 52 | 43 | 0 | 0 | 0 | 12a |
| Wheat | 99 | 96 | 97 | 33b | 65 | 48 | 0 | 11 | 0 | 3b |

[a]The proportion of seeds that had germinated and showed stroma of *P. semeniperda*.
[b]The proportion of seeds that were ungerminated and showed stroma of *P. semeniperda*.

February 1993 harvest. *B. diandrus* seeds harvested in February had significantly reduced germination and emergence when compared to uninoculated controls (P<0.01) (Table 12). All seeds derived from inoculated plants that did not germinate had stomatal development at the embryo end of the caryopses. The coleoptile lengths of seedlings derived from seed harvested from inoculated and uninoculated plants were not significantly different. Seeds harvested in January 1993 were incubated under conditions of high humidity (99% RH) for a month and assayed. A similar pattern of germination and emergence rates were observed after incubation. No significant difference (P>0.05) were observed between the seeds harvested in February 1993 and the seeds harvested in January 1993 that were incubated at 99% humidity with any of the parameters tested.

Infection maps. A significantly larger proportion of florets were infected in inflorescence position 1 (0.80 SE 0.04) than either inflorescence position 2 (0.59, SE 0.03) or inflorescence position 3 (0.57, SE 0.04). No statistical difference was observed between inflorescence positions 2 or 3.

TABLE 12

The effect of inoculation of field grown *B. diandrus* with *P. semeniperda* on caryopses germination and development:
1. When caryopses were harvested in February 1993 and
2. When caryopses were harvested in January 1993 and incubated at 99% relative humidity for 1 month. Significant differences (P > 0.01) were observed between uninoculated (U) and inoculated (I) caryopses in all parameters tested except coleoptile length. No significant differences were found between harvest dates (P > 0.05). Data are means of 4 replicates and duplicate CR bioassays.

| Harvest | % Germ | | % Emerge | | Col length (mm) | | % Stroma | |
|---|---|---|---|---|---|---|---|---|
| | U | I | U | I | U | I | U | I |
| Feb. 1993 | 98 | 27 | 96 | 26 | 49 | 43 | 0 | 73 |
| Jan. 1993 | 95 | 31 | 93 | 28 | 47 | 45 | 0 | 69 |

Trials of different inoculum types

Infection levels of *B. diandrus* seeds growth in the 1993/94 season were lower than the 1994/95 season (Table 13). Infection of wheat (measured as stromatal development) only occurred when inflorescences were inoculated with conidial suspensions and ranged from 5 to 8%, slightly more than levels of infection in the controls (3%). No differences were observed for other infection parameters tested. The greatest level of infection, when expressed as the proportion of seeds with stromatal development of *P. semeniperda*, occurred in both seasons when florets of *B. diandrus* were inoculated with conidia. No significant differences were observed between infection levels in *B. diandrus* seeds when florets were infected one or more times with conidai. Statistically similar infection levels of seeds was observed whether florets were inoculated with conidia in an aqueous suspension or in a suspension of toxic culture filtrate. Inoculation of florets with mycelium of *P. semeniperda* resulted in 10 to 13% infection of seeds. Slightly higher levels of infection were observed when mycelium was suspended in a sucrose solution. In general, seeds of *B. diandrus* which showed stromatal development of *P. semeniperda* failed to germinate.

TABLE 13

Different inoculum types of *P. semeniperda* used to inoculate field grown *B. diandrus* and their effect on caryopses germination and development, when caryopses were harvested in January 1994 and 1995. Data followed by a different letter in the same column were significantly different (P > 0.05). Data are means of 4 replicates and duplicate CR bioassays. Data were not pooled for separate trials because heterogeneity of variances was detected with Bartlett's test.

| Inoculum type | % Germ 94 | % Germ 95 | % Emerge 94 | % Emerge 95 | Col length 94 | Col length 95 | Germinated seeds with Stroma[a] 94 | Germinated seeds with Stroma[a] 95 | Ungerminated seeds with Stroma[b] 94 | Ungerminated seeds with Stroma[b] 95 |
|---|---|---|---|---|---|---|---|---|---|---|
| Myc[c] | 88b | | 80b | | 55a | | 2 | | 12b | |
| Myc + Suc | 87b | 90b | 78b | 83b | 52a | 54a | 4 | 1b | 13b | 10b |
| Alginate[c] | 92a | | 86b | | 51a | | 0 | | 8b | |
| Conidia 1 | 86b | 65c | 74b | 60c | 43b | 44b | 4 | 5a | 14b | 35c |
| Conidia 2 | 87b | 60c | 80b | 54c | 47ab | 45b | 3 | 3ab | 13b | 40c |
| Conidia 3 | 87b | 65c | 83b | 57c | 47ab | 44b | 1 | 3ab | 13b | 35c |
| Conidia 4 | 86b | 83c | 85b | 53c | 45b | 43b | 0 | 4a | 14b | 77c |
| Con + toxin[d] | | 68c | | 59c | | 43b | | 5a | | 32c |
| Toxin filtrate[d] | | 96a | | 95a | | 54a | | 1b | | 3a |
| Uninoc | 97a | 96a | 96a | 98a | 52a | 58a | 0 | 0 | 3a | 2a |

[a]The proportion of seeds that has germinated and showed stroma of *P. semeniperda*.
[b]The proportion of seeds that were ungerminated and showed stroma of *P. semeniperda*.
[c]These treatments were only trialed in the 1993/94 season.
[d]These treatments were only trialed in the 1994/95 season.

Inoculation of *B. diandrus* florets with conidia of *P. semeniperda* had a significant deleterious effect on germination of seeds and emergence and coleoptile lengths of seedlings when compared to uninoculated controls.

The incorporation of mycelium into pellets obtaining alginate resulted in 8% of seeds showing stromatal developments of *P. semeniperda*.

Inoculation of six grass species

Inoculation of *B. diandrus, L. rigidum, H. leporinum* and *V. bromoides* florets with conidia of *P. semeniperda* resulted in significantly lower germination of seeds than uninoculated controls (P<0.05) (Table 14). Seedling emergence and coleoptile lengths were significantly reduced for all inoculated grass species.

TABLE 14

The effect of inoculation of field grown grass species with *P. semeniperda* on caryopses germination and development, when caryopses were harvested in December 1993. Data followed by a common letter in the same column are not significantly different (P > 0.05) according to Tukey's HSD test. Data that are in bold italicised type within species and infection parameter are significantly different (P > 0.05). Data are means of 4 replicates and duplicate CR bioassays.

| Species | % Germ U | % Germ I | % Emerge U | % Emerge I | Col length U | Col length I | Germinated seeds with Stroma[a] U | Germinated seeds with Stroma[a] I | Ungerminated seeds with Stroma[b] U | Ungerminated seeds with Stroma[b] I |
|---|---|---|---|---|---|---|---|---|---|---|
| T. aestivum | 96 | 94 | 96 | 41 | 47 | 31 | 0 | 15b | 4 | 6 |
| B. diandrus | 95 | 60a | 95 | 44 | 58 | 43 | 0 | 22c | 5 | 40c |
| A. fatua | 58 | 56 | 58 | 47 | 52 | 47 | 0 | 5a | 2 | 3 |
| L. rigidum | 86 | 74b | 76 | 64 | 50 | 39 | 0 | 12b | 3 | 60 |
| H. leporinum | 94 | 79b | 92 | 54 | 50 | 35 | 0 | 24c | 3 | 14b |
| V. bromoides | 98 | 82b | 98 | 28 | 35 | 16 | 0 | 43d | 4 | 16b |

[a]The proportion of seeds that has germinated and showed stroma of *P. semeniperda*.
[b]The proportion of seeds that were ungerminated and showed stroma of *P. semeniperda*.

A significantly larger proportion of *B. diandrus* seeds showed development of stromata and did not germinate than any other grass species. *B. diandrus* also had the greatest total infection species when expressed as seeds developing stromata. *H. leporinum* and *V. bromoides* both had levels of infection significantly higher than wheat. *A. fatua* had significantly lower levels of infection than wheat.

Discussion

The field studies reported in this Example provide evidence for the use of *P. semeniperda* as a mycoherbicide. In all field trials, inoculation of florets at anthesis resulted in decreased germination, emergence and coleoptile lengths of mature seeds and seedlings. Infected seeds of all species of grass inoculated in the field trials were characterised by the formation of vegetative stromata and a reduction in coleoptile length of the resultant seedling.

The field trial conducted in 1992/93 was harvested twice with contrasting results. The seeds of *B. diandrus* that were harvested at maturity (January 1993) had a far smaller proportion (12%) of seeds exhibiting stromata of *P. semeniperda* than those harvested one month later (73%, February 1993). The reason for this difference is uncertain, although it is possible that it was due to the effects of humidity on the development of the pathogen within the seed. Above average rainfall (207 mm) which occurred at the field site during January 1993 (average 105 mm) resulted in very humid weather conditions. Evidence for this theory was provided by placing seeds collected in the January 1993 harvest under conditions of high humidity (95–99% RH) and repeating the CR bioassay. The placement of the early harvested seed under conditions of high humidity resulted in levels of infection statistically similar to those in late harvested seed. It is postulated therefore, that some mechanism of 'fungal after-ripening' which is correlated with humidity exists in the *P. semeniperda-B. diandrus* pathosystem.

REFERENCES

Hagbor, W. A. F. (1970). A device for injecting solutions and suspensions into thin leaves of plants. *Conadian Journal of Botany* 48, 1135–1136.

Hargreaves, J. A. (1982). The nature of the resistance of oat leaves to infection by *Pyrenophora teres*. *Physiological Plant Pathology* 20, 165–171.

Keane, P. J., Limongiello, N. & Warren, M. A (1988). A modified method for clearing and staining leaf-infecting fungi in whole leaves. *Australasian Plant Pathology* 17, 37–38.

Lawrence, E. B., Nelson, P. E. & Ayers, J. E. (1981). Histopathology of sweet corn seed and plants infected with *Fusarium moniliforme* and *F. oxysporum Phytopathology* 71, 379–386.

Medd, R. W. (1992). Directions for biohorbicide research in Australia. *Plant Protection quarterly*. 7, 151–153.

Sivanesan, A. (1987). Graminicolous species of Bipolaris, Curvularia, Drechslera, Exserohilum and their teleomorphs. Mycological Papers No. 158, C.A.B. International Oxon.

Snedecor, G. W. & Cochran, W. G. (1989). *Statistical Methods* 8th edition. Iowa State University Press, Ames.

Tomás, A. & Bockus, W. W. (1987). Cultivar-specific toxity of culture filtrates of Pyrenophora tritici-repentis. *Phytopathology* 77, 1337–1340.

Walker, H. L. and Connick, W. J. (1983). Sodium alginate for production and formulation of mycoherbicides. *Weed Science* 31, 333–338.

Wilkinson, L., Hill, M., Welna, J. P. and Birkenbeuel, G. K. (1992). *SYSTAT for Windows: statistics, Version 5 Edition,* Systat, Inc. Evanston, Ill.

Zadoks, J. C., Chang, T. T. & Konzak, C. F. (1974). A decimal code for the growth stages of cereals. *Weed Research* 14, 415–421.

It will be appreciated by persons skilled in the art that numerous variations and/or modifications may be made to the invention as shown in the specific embodiments without departing from the spirit or scope of the invention as broadly described. The present embodiments are, therefore, to be considered in all respects as illustrative and not restrictive.

We claim:

1. A method for controlling the proliferation of annual grass weeds in an area, comprising applying to said area a composition comprising;

(i) one or more species of Pyrenophora fungi and/or their anamorphs and/or (ii) a toxin(s) or toxin(s)-containing preparation derived from one or more species of Pyrenophora fungi and/or their anamorphs, and an agriculturally acceptable carrier.

2. A method according to claim 1, wherein said Pyrenophora fungi(us) is selected from *P. semeniperda, P. teres* and a mixture thereof.

3. A method according to claim 2, wherein said Pyrenophora fungi(us) is *P. semeniperda.*

4. A method according to claim 3, wherein said Pyrenophora fungi(us) is *P. semeniperda* isolate DAR71761.

5. A method according to claim 2, wherein said composition comprises conidia.

6. A method according to claim 5, wherein said composition is a conidial suspension of about $1 \times 10^3$ to $8 \times 10^4$ conidia $ml^{-1}$.

7. A method according to claim 6, wherein said composition is a conidial suspension of about $2.5 \times 10^4$ to $7.5 \times 10^4$ conidia $ml^{-1}$.

8. A method according to claim 2, wherein said composition comprises an effective concentration of a mycelial homogenate.

9. A method according to claim 8, wherein said composition is encased in a dissolvable solid carrier.

10. A method according to claim 9, wherein said carrier is alginate.

11. A method according to claim 2, wherein said composition comprises about 25 g $L^{-1}$ of hyphae.

12. A method according to claim 6, wherein said composition is applied to the area at amounts of 250 ml $m^{-2}$.

13. A method according to claim 12, wherein the composition is applied whilst 35% or more of the total annual grass weeds in the area are in anthesis (GS55 to GS75).

14. A method according to claim 13, wherein the composition is applied whilst 50% or more of the total annual grass weeds in the area are in anthesis (GS55 to GS75).

15. A method according to claim 12, wherein the composition is applied whilst 35% or more of any one target annual grass weed species in the area are in anthesis (GS55 to GS75).

16. A method according to claim 15, wherein the composition is applied whilst 50% or more of any one target annual grass weed species in the area are in anthesis (GS55 to GS75).

17. A method according to claim 2, wherein the annual grass weeds are selected from the group consisting of annual ryegrass, brome species, barley grass and vulpia.

18. A method according to claim 2, wherein said area includes adult crop plants.

19. A method according to claim 6, wherein the composition further comprises a surfactant(s) and/or a wetting agent(s).

20. A method for producing a Pyrenophora toxin(s) or toxin(s)-containing preparation comprising, growing one or more species of Pyrenophora fungi in culture with agitation.

21. A method according to claim 20, wherein said Pyrenophora fungi(us) is *P. semeniperda, P. teres* or a mixture thereof.

22. A method according to claim 21, wherein said Pyrenophora fungi(us)is *P. semenipersa* isolate DAR71761.

* * * * *

UNITED STATES PATENT AND TRADEMARK OFFICE

CERTIFICATE OF CORRECTION

PATENT NO. : 6,008,159
DATED : December 28, 1999
INVENTOR(S) : MEDD et al

It is certified that error appears in the above-identified patent and that said letters patent is hereby corrected as shown below:

On the title page, after "[73] Assignee:" insert the following additional assignee: Grains Research and Development Corporation, Level 2, Bligh House, National Circuit, Barton, Australian Capital Territory, Australia 2600.

Signed and Sealed this

Twenty-seventh Day of March, 2001

*Attest:*

NICHOLAS P. GODICI

*Attesting Officer*  *Acting Director of the United States Patent and Trademark Office*